United States Patent
Mersch

(10) Patent No.: US 9,295,854 B2
(45) Date of Patent: Mar. 29, 2016

(54) LIGHT AND BIOELECTRIC THERAPY PAD

(71) Applicant: Steven H. Mersch, Germantown, OH (US)

(72) Inventor: Steven H. Mersch, Germantown, OH (US)

(73) Assignee: Point Source, Inc., Germantown, OH (US)

( * ) Notice: Subject to any disclaimer, the term of this patent is extended or adjusted under 35 U.S.C. 154(b) by 0 days.

(21) Appl. No.: 13/795,385

(22) Filed: Mar. 12, 2013

(65) Prior Publication Data

US 2014/0148879 A1    May 29, 2014

Related U.S. Application Data

(60) Provisional application No. 61/730,653, filed on Nov. 28, 2012.

(51) Int. Cl.
*A61N 1/36* (2006.01)
*A61N 5/06* (2006.01)
(Continued)

(52) U.S. Cl.
CPC ............ *A61N 5/0613* (2013.01); *A61N 1/0476* (2013.01); *A61N 1/0492* (2013.01);
(Continued)

(58) Field of Classification Search
CPC ........... A61N 1/04; A61N 5/06; A61B 19/00; H01M 10/44; H01L 29/18; G05F 1/00; G02B 6/26; F21S 4/00; F21V 13/00; F21V 19/00
USPC ................. 607/88; 128/898; 315/291, 185 S; 320/102; 385/38; 257/14, 88; 362/249.02, 249.05, 364, 231
See application file for complete search history.

(56) References Cited

U.S. PATENT DOCUMENTS 4,009,051 A * 2/1977 Kazis et al. ............. 320/102
4,675,575 A    6/1987 Smith et al.
(Continued)

FOREIGN PATENT DOCUMENTS

RU    2153366     7/2000
RU   12465025    10/2012

OTHER PUBLICATIONS

Alternating current Collins English Dictionary—Complete and Unabridged © HarperCollins Publishers 1991, 1994, 1998, 2000, 2003.*

(Continued)

*Primary Examiner* — Gary Jackson
*Assistant Examiner* — Victor Shapiro
(74) *Attorney, Agent, or Firm* — Hasse & Nesbitt LLC; Daniel F. Nesbitt

(57) ABSTRACT

A light and bioelectric therapy pad that delivers light and bioelectric stimulation to adjacent tissue. The therapy pad includes an electrical tracing circuit containing elongated, parallel and spaced-apart approximate linear tracings (ALT) that provide current flow in opposite directions along the ALT during alternating positive and negative drive cycles of an alternating current (AC) supply. The ALT includes first and second header tracings wired to a row of light emitting diodes (LEDs), with the anodes of a first group of LEDs wired to the first header tracing, and the anodes of the remaining LEDs wired to the second header tracing. The ALTs are wired into the circuit with current flowing to the first header tracing at one end of the row of LEDs, and to the second header tracing at the opposite end, so that adjacent ALT provide current flow in opposite directions during both positive and negative drive cycles.

17 Claims, 20 Drawing Sheets

(51) Int. Cl.
*A61N 1/04* (2006.01)
*A61N 1/32* (2006.01)

(52) U.S. Cl.
CPC ........... *A61N 1/326* (2013.01); *A61N 1/36014* (2013.01); *A61N 2005/0645* (2013.01); *A61N 2005/0652* (2013.01)

(56) References Cited

U.S. PATENT DOCUMENTS

| | | | |
|---|---|---|---|
| 5,685,837 A | 11/1997 | Horstmann | |
| 5,913,883 A | 6/1999 | Alexander et al. | |
| 5,997,569 A | 12/1999 | Chen et al. | |
| 6,069,452 A * | 5/2000 | Rossner | H05B 37/036 315/135 |
| 6,096,066 A | 8/2000 | Chen et al. | |
| 6,290,713 B1 * | 9/2001 | Russell | A61N 5/0616 607/88 |
| 6,350,275 B1 * | 2/2002 | Vreman et al. | 607/88 |
| 6,471,716 B1 | 10/2002 | Pecukonis | |
| 6,569,189 B1 | 5/2003 | Augustine et al. | |
| 6,584,359 B1 | 6/2003 | Motoi | |
| 6,596,016 B1 * | 7/2003 | Vreman et al. | 607/88 |
| 6,602,275 B1 * | 8/2003 | Sullivan | 607/88 |
| 6,641,599 B2 | 11/2003 | Peterson et al. | |
| 6,645,230 B2 * | 11/2003 | Whitehurst | 607/88 |
| 6,676,655 B2 | 1/2004 | McDaniel | |
| 6,811,563 B2 * | 11/2004 | Savage et al. | 607/88 |
| 6,861,570 B1 | 3/2005 | Flick | |
| 7,009,199 B2 * | 3/2006 | Hall | 257/14 |
| 7,038,399 B2 | 5/2006 | Lys et al. | |
| 7,052,167 B2 | 5/2006 | Vanderschuit | |
| 7,084,389 B2 | 8/2006 | Spector | |
| 7,117,034 B2 | 10/2006 | Kronberg | |
| 7,210,817 B2 | 5/2007 | Lee et al. | |
| 7,210,819 B2 * | 5/2007 | Jiang et al. | 362/249.02 |
| 7,264,381 B2 * | 9/2007 | Liu et al. | 362/364 |
| 7,274,844 B2 * | 9/2007 | Walt et al. | 385/38 |
| 7,420,332 B2 * | 9/2008 | Kato | H05B 33/0821 315/185 S |
| 7,438,719 B2 * | 10/2008 | Chung et al. | 607/88 |
| 7,457,667 B2 | 11/2008 | Skiba | |
| 7,559,945 B2 | 7/2009 | Breden et al. | |
| 7,662,176 B2 | 2/2010 | Skiba et al. | |
| 7,672,719 B2 | 3/2010 | Skiba et al. | |
| 7,813,806 B2 | 10/2010 | Skiba | |
| 7,847,487 B2 * | 12/2010 | Kato | H05B 33/0803 315/185 S |
| 7,904,147 B2 | 3/2011 | Schneider et al. | |
| 7,921,853 B2 * | 4/2011 | Fiset | 128/898 |
| 7,922,676 B2 | 4/2011 | Daskal et al. | |
| 7,976,191 B2 * | 7/2011 | Gibboney | 362/249.05 |
| 8,076,867 B2 * | 12/2011 | Kuo et al. | 315/291 |
| 8,188,489 B2 * | 5/2012 | Lee et al. | 257/88 |
| 8,202,307 B2 * | 6/2012 | Rodrigues et al. | 607/88 |
| 8,206,014 B2 | 6/2012 | Allen | |
| 2002/0143373 A1 | 10/2002 | Courtnage et al. | |
| 2003/0125782 A1 | 7/2003 | Streeter | |
| 2005/0085875 A1 * | 4/2005 | Van Zuylen | 607/88 |
| 2005/0148996 A1 | 7/2005 | Sun et al. | |
| 2006/0173514 A1 | 8/2006 | Biel et al. | |
| 2006/0206173 A1 | 9/2006 | Gertner et al. | |
| 2006/0217787 A1 | 9/2006 | Olson et al. | |
| 2007/0129776 A1 | 6/2007 | Robins et al. | |
| 2007/0135874 A1 | 6/2007 | Bala | |
| 2007/0233208 A1 | 10/2007 | Kurtz et al. | |
| 2007/0276457 A1 | 11/2007 | Gordon | |
| 2009/0060886 A1 | 3/2009 | Alt | |
| 2009/0240310 A1 | 9/2009 | Kennedy | |
| 2011/0310601 A1 * | 12/2011 | Shao | F21S 4/001 362/231 |
| 2012/0041521 A1 | 2/2012 | Oron et al. | |
| 2012/0068085 A1 | 3/2012 | Cucin | |

OTHER PUBLICATIONS

Biot-Savart Law. http://www.magnet.fsu.edu/ Web site of © 1995-2013 National High Magnetic Field Laboratory • 1800 E. Paul Dirac Drive, Tallahassee, FL 32310-3706.*

Diode The American Heritage® Science Dictionary Copyright © 2005 by Houghton Mifflin Company. Published by Houghton Mifflin Company. All rights reserved.*

PCT/US2013/072164 International Search Report and Written Opinion dated Mar. 6, 2014 (7 pages).

Anderson, R., et al., "The Optics of Human Skin". J Invest Dermatol, Jul. 1981, vol. 77, Issue 1, pp. 13-19. (7 pages).

Blount, A., et al., "The Use of Bioelectric Dressings in Skin Graft Harvest Sites: A Prospective Case Series". J Burn Care Res, May-Jun. 2012, vol. 33, Issue 3, pp. 354-357. (4 pages).

Fitzgerald, M., et al., "Near Infrared Light Reduces Oxidative Stress and Preserves Function in CNS Tissue Vulnerable to Secondary Degeneration Following Partial Transection of the Optic Nerve". J Neurotrauma, Nov. 2010, vol. 27, Issue 11, pp. 2107-2119. Published online Sep. 7, 2010. (Abstract only—1 page).

Hamblin, M., et al., "Low-level Light Therapy Aids Traumatic Brain Injury". SPIE Newsroom May 5, 2011. doi:10.1117/2.1201102.003573 (3 pages).

Hou, J., et al., "In Vitro Effects of Low-level Laser Irradiation for Bone Marrow Mesenchymal Stem Cells: Proliferation, Growth Factors Secretion and Mycogenic Differentiation". Lasers Surg Med, Dec. 2008, vol. 40, Issue 10, pp. 726-733. Published online Dec. 8, 2008. (8 pages).

Kloth, L., "Electrical Stimulation for Wound Healing: A Review of Evidence from In Vitro Studies, Animal Experiments, and Clinical Trials". Lower Extremity Wounds, Mar. 2005, vol. 4, Issue 1, pp. 23-44. (22 pages).

Naeser, M., et al., "Transcranial LED Therapy for Cognitive Dysfunction in Chronic, Mild Traumatic Brain Injury: Two Case Reports". Mechanisms for Low-Light Therapy V, Hamblin, M., et al., (ed.), Proc. SPIE, Feb. 25, 2010, vol. 7552, 75520L, doi:10.1117/12.842510. (13 pages).

Naeser, M., et al., "Improved Cognitive Function After Transcranial, Light-Emitting Diode Treatments in Chronic, Traumatic Brain Injury: Two Case Reports". Photomed Laser Surg, May 2011, vol. 29, Issue 5, pp. 351-358. (10 pages).

Naeser, M., et al., "Potential for Transcranial Laser or LED Therapy to Treat Stroke, Tramatic Brain Injury, and Neurodegenerative Disease". Photomed Laser Surg. Jul. 2011, vol. 29, Issue 7, pp. 443-446. (4 pages).

Oron, U., "Light Therapy and Stem Cells: A Therapeutic Intervention of the Future". Interv Cardiol, Dec. 2011, vol. 3, Issue 6, pp. 627-629. (3 pages).

Parker, I., et al., "The Treatment of Partial Thickness Burns with a Bioelectric Dressing Following Cosmetic Laser Facial Resurfacing". Proceedings of the American Burn Association, 41st Annual Meeting, J Burn Care Res (Supp), Mar. 2009, vol. 30, No. 2, Abstract No. 171, p. S129. (1 page).

Vomaris Innovations, Inc., "Scientific Summary: Procellera with Prosit: A Novel Bioelectrical Dressing". Oct. 2011, (11 pages).

Tuby, H., et al., "Induction of Autologous Mesenchymal Stem Cells in the Bone Marrow by Low-level Laser Therapy. Has Profound Beneficial Effects on the Infarcted Rat Heart". Lasers Surg Med, Jul. 2011, vol. 43, Issue 5, pp. 401-409. Published online Jun. 14, 2011. (9 pages).

Wu, Q., et al., "Low Level Laser Therapy for Traumatic Brain Injury". Mechanisms for Low-Light Therapy V, Hamblin, M., et al., (ed.), Proc. SPIE, Feb. 17, 2010, vol. 7552, 755206, doi:10.1117/12.841014. (9 pages).

DeLong, J., et al., "The Use of Current Generating Dressings Under Negative Pressure". Poster presented at The Symposium on Advanced Wound Care, 2010 (http://rx.procellera.com/u/files/ce-at-001.pdf). (1 page).

Elizondo, J., "The Management of Complex Wounds with the Use of a Bioelectric, Antimicrobial Dressing". Poster presented at The Sym-

(56) References Cited

OTHER PUBLICATIONS posium on Advanced Wound Care, 2009 (http://rx.procellera.com/u/files/ce-cow-the-mgmt-of-complex-wounds-with-bioelectric-dressing-sawc-2009.pdf). (1 page).

Gubermann, R., "Preliminary Study Findings: Faster Wound Closure is Achieved When the Bioelectric Dressing is Used as an Adjunct to Negative Pressure Wound Therapy". Poster presented at The Symposium on Advanced Wound Care, 2010 (http://rx.procellera.com/u/files/ce-at-002.pdf). (1 page).

McCoy, J., "Limb Salvage Through the Use of a Bioelectric, Sntimicrobial Dressing". Poster presented at The Symposium on Advanced Wound Care, 2009 (http://rx.procellera.com/u/files/ce-cow-limb-salvage-with-bioelectric-dressing-sawc-2009.pdf). (1 page).

Perez, R., et al., "Assessment of the Effects on Wound Healing and Gene Expression of a Bio-Electric Dressing (CMB) Using a Porcine Wound Model and Real Time RT-PCR". Poster presented at the 67th Annual Meeting of the American Academy of Dermatology, J Am Acad Dermatol, Mar. 2009, vol. 60, Issue 3 (Supp 1), p. AB200. (http://rx.procellera.com/u/files/ce-s-assessment-of-the-effects-on-wound-healing-and-gene-expression-of-bio-electric-dressing-2009-aad.pdf). (1 page).

Sheftel, S., et al., "A Comparison of Bioelectric Wound Dressings vs. Standard Silver Dressings". Poster presented at the Clinical Symposium on Advances in Skin and Wound Care, Oct. 2009. (1 page).

Sheftel, S., et al., "Bioelectric vs. Standard Wound Care: A Randomized Comparative Study". Poster presented at The Symposium on Advanced Wound Care, 2009 (http://rx.procellera.com/procellera/clinical-evidence). (1 page).

Sheftel, S., "The Role of a Bio-electric, Antimicrobial Dressing in the Healing of Acute and Chronic Wounds". Poster presented at the Symposium on Advanced Wound Care, 2008 (http://rx.procellera.com/u/files/ce-aw-005.pdf). (1 page).

Tallis, A., et al., "Charge Your Wounds, A Novel Bioelectric Dressing for Non-Healing Wounds". Poster presented at The Symposium on Advanced Wound Care, 2009 (http://rx.procellera.com/u/files/ce-cw-003.pdf). (1 page).

\* cited by examiner

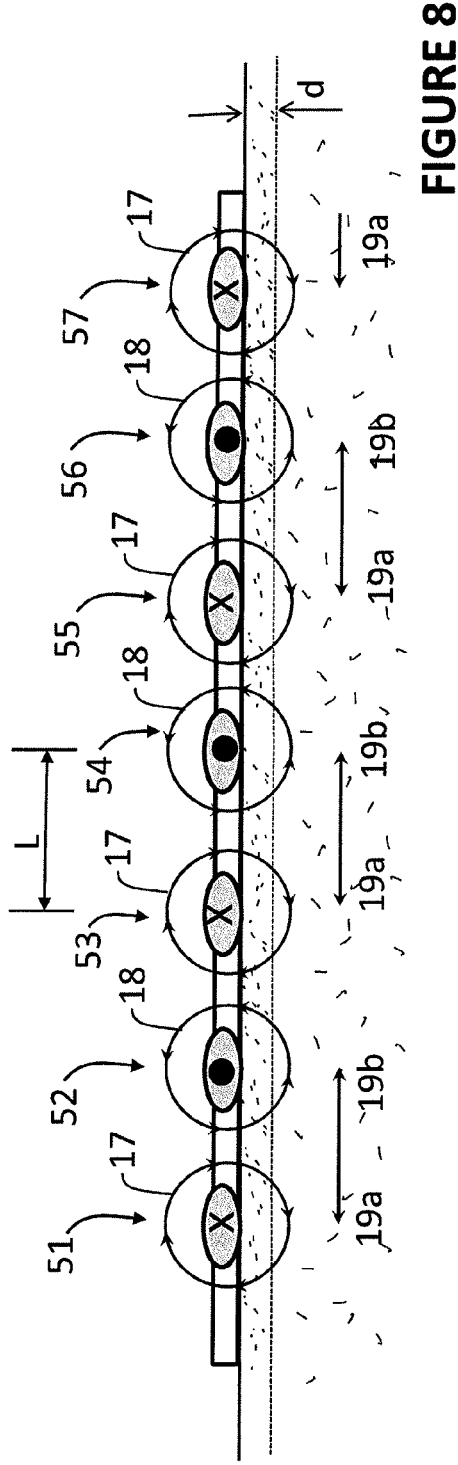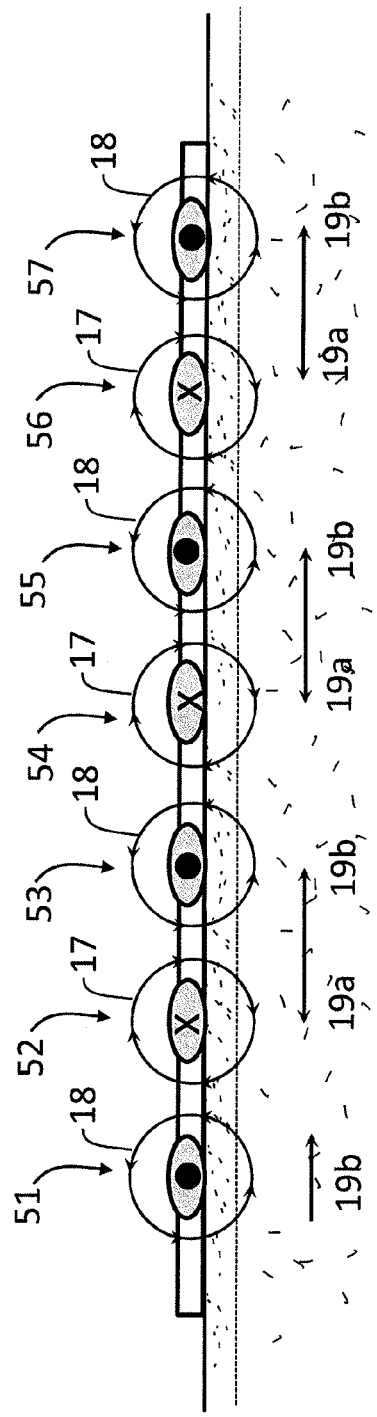

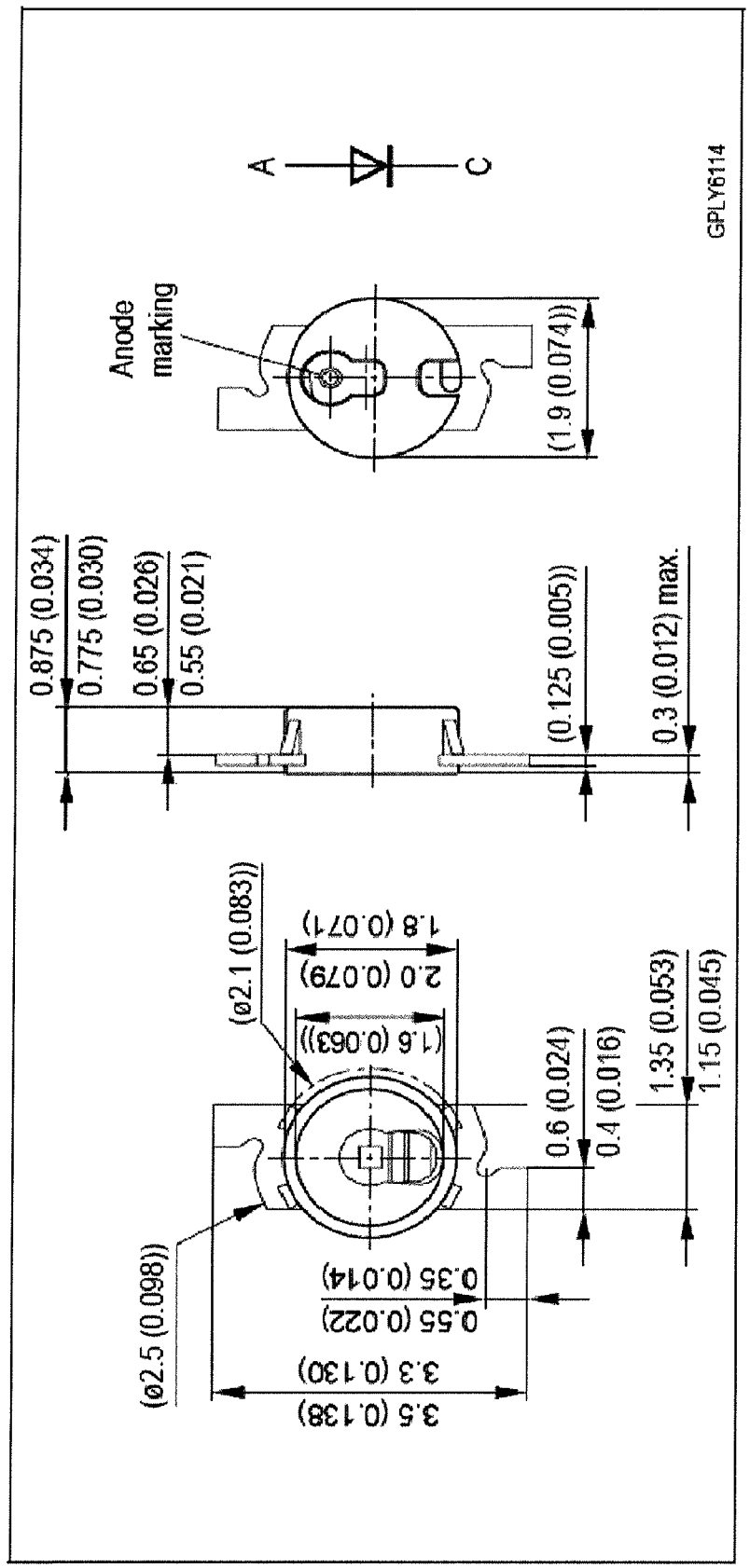
FIGURE 15 - Prior Art

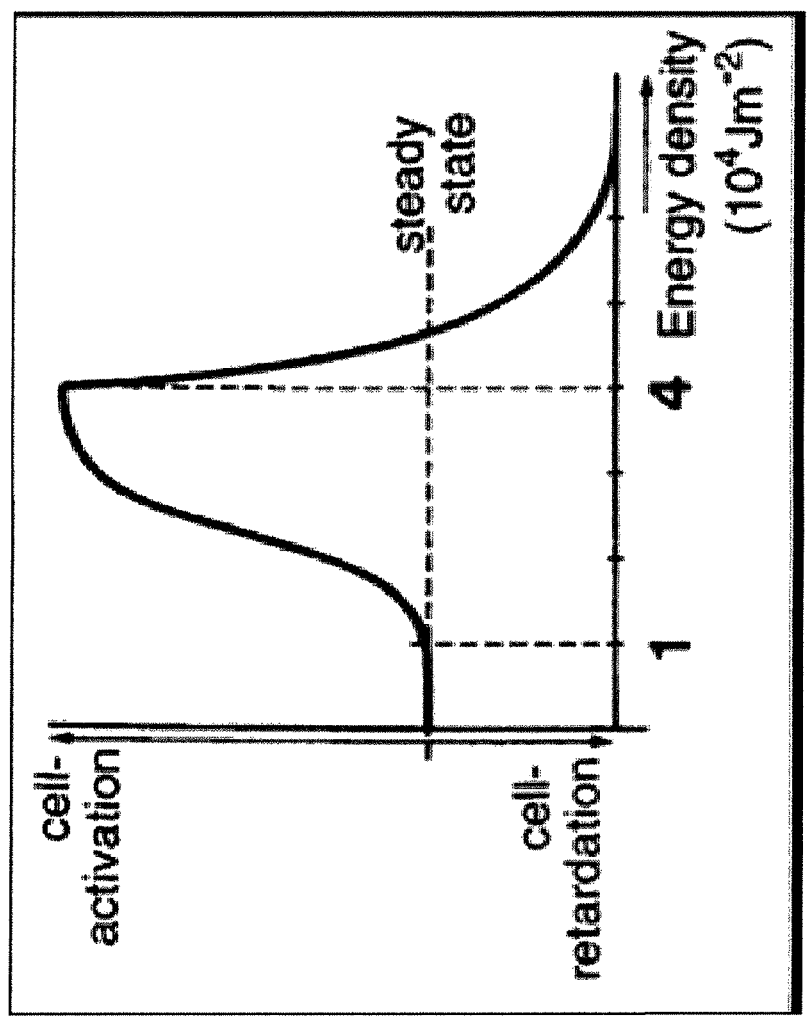
FIGURE 16A – Prior Art

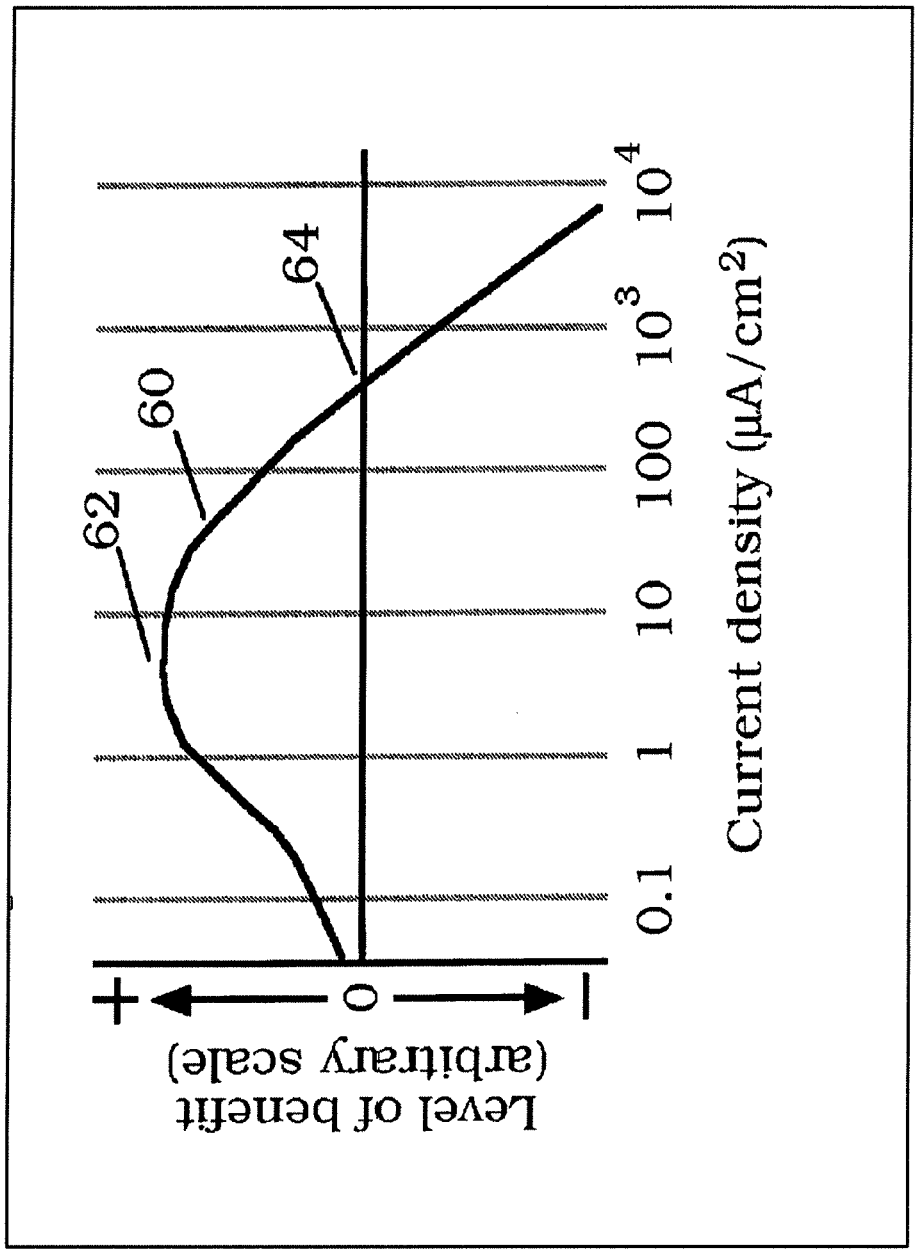
FIGURE 16B – Prior Art

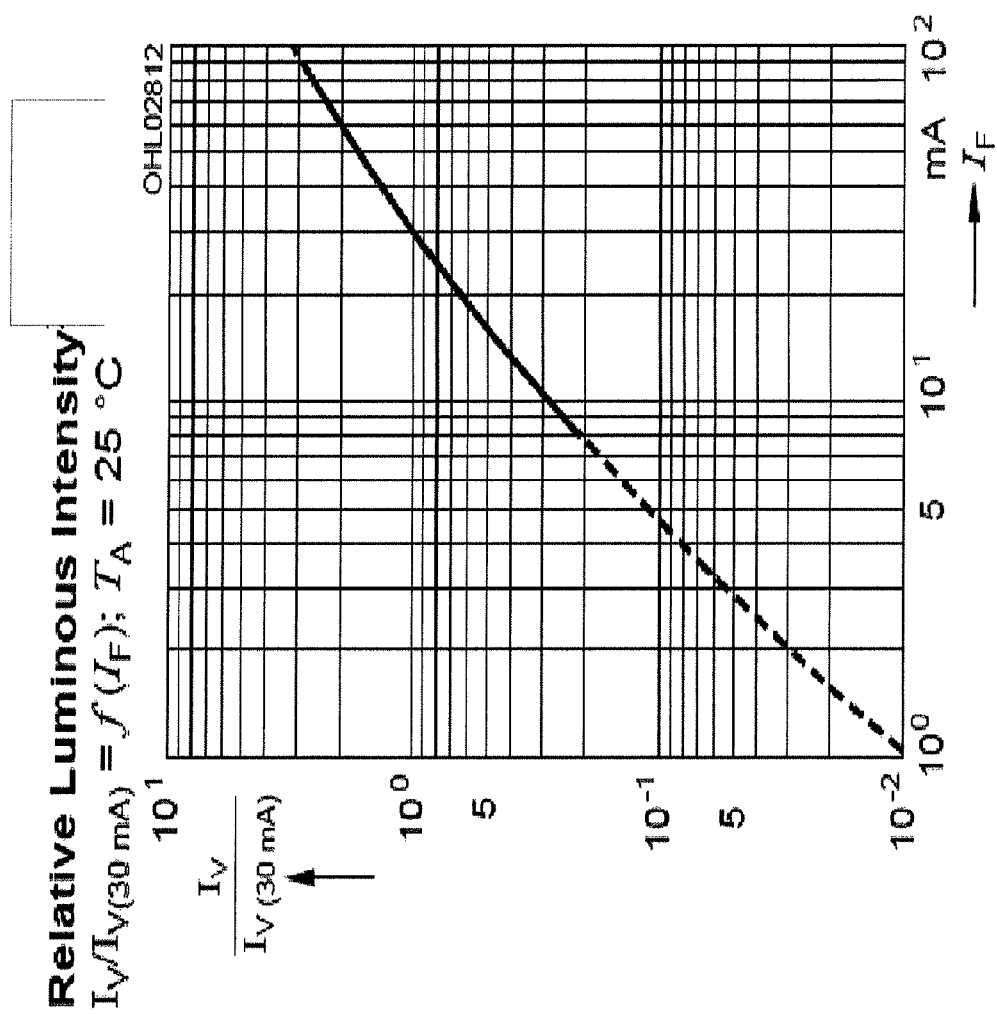
FIGURE 17 - Prior Art

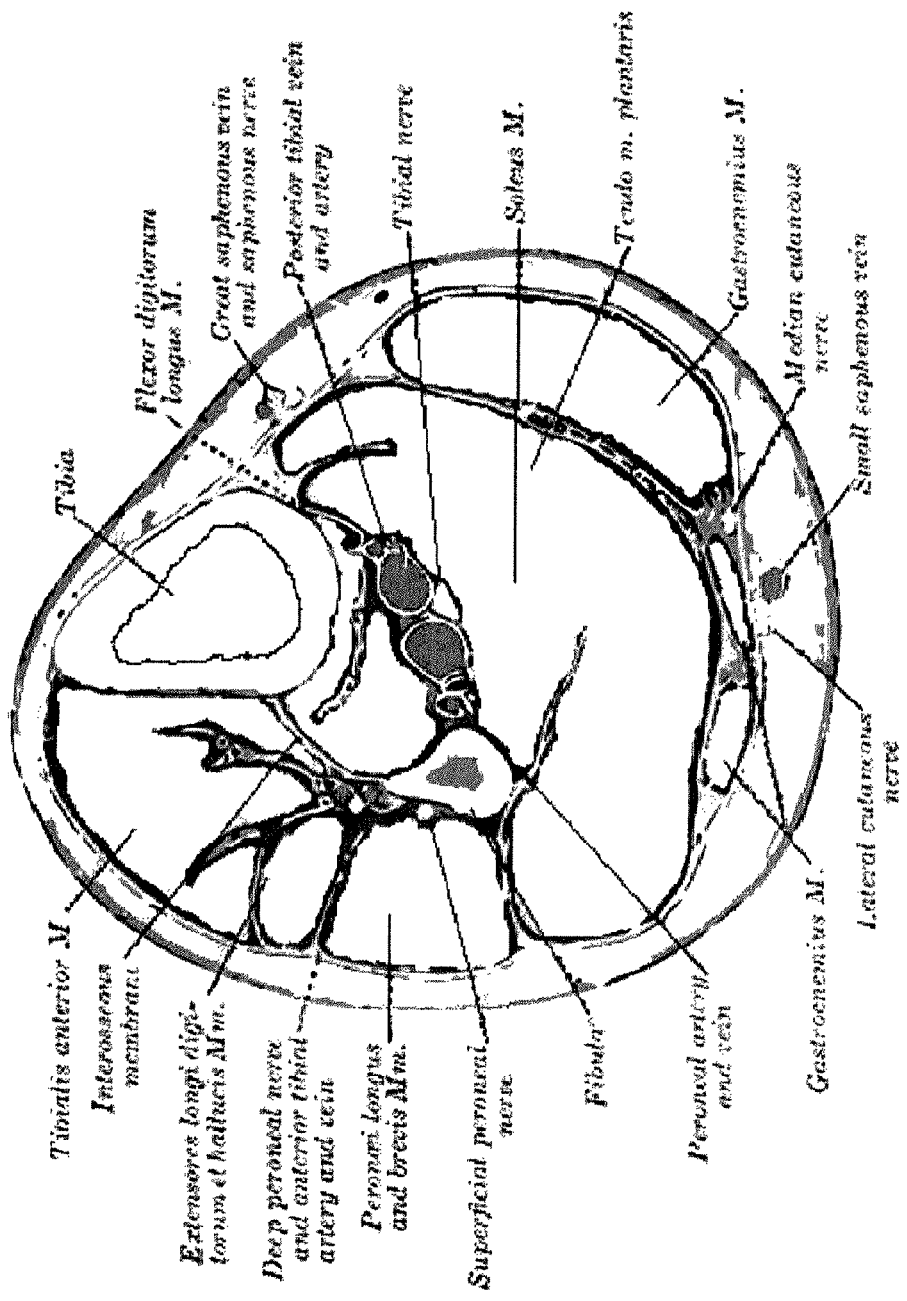
FIGURE 19 - Prior Art

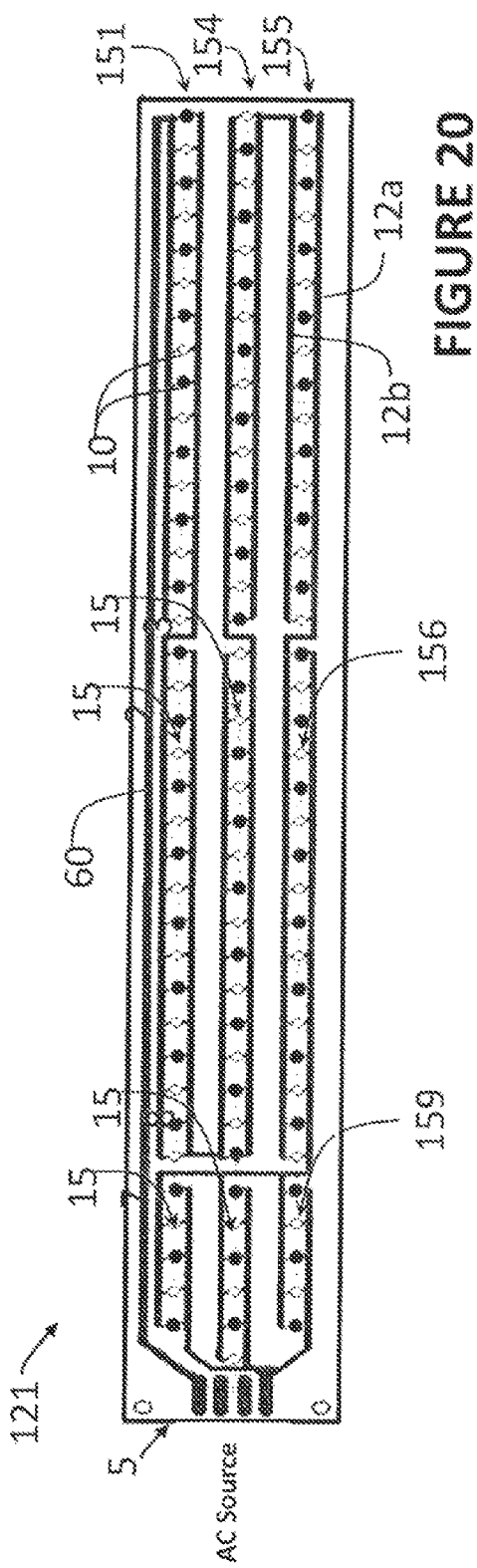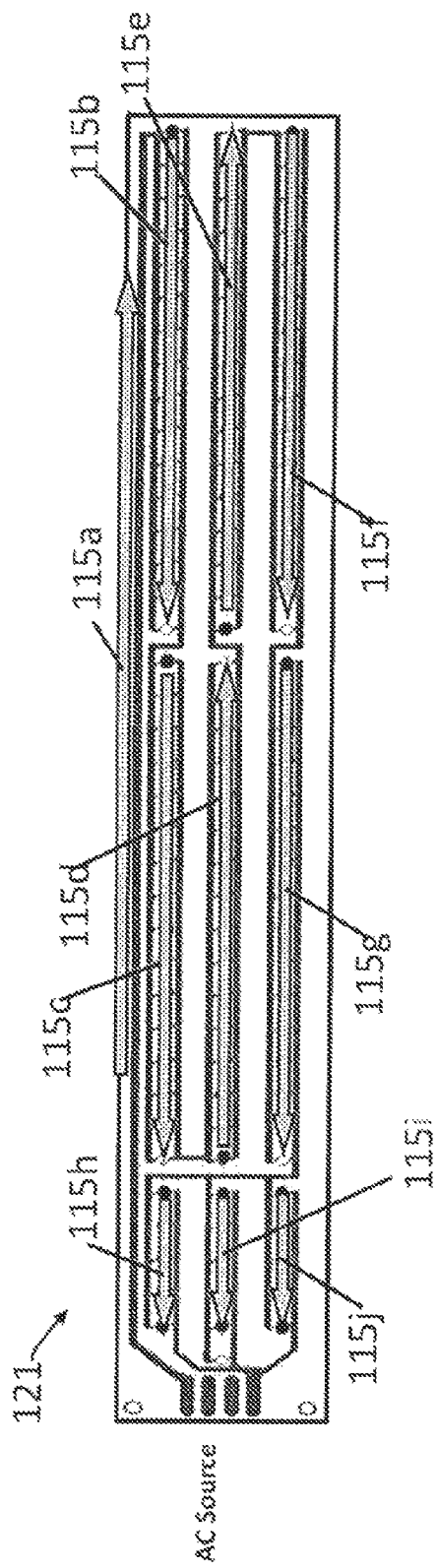

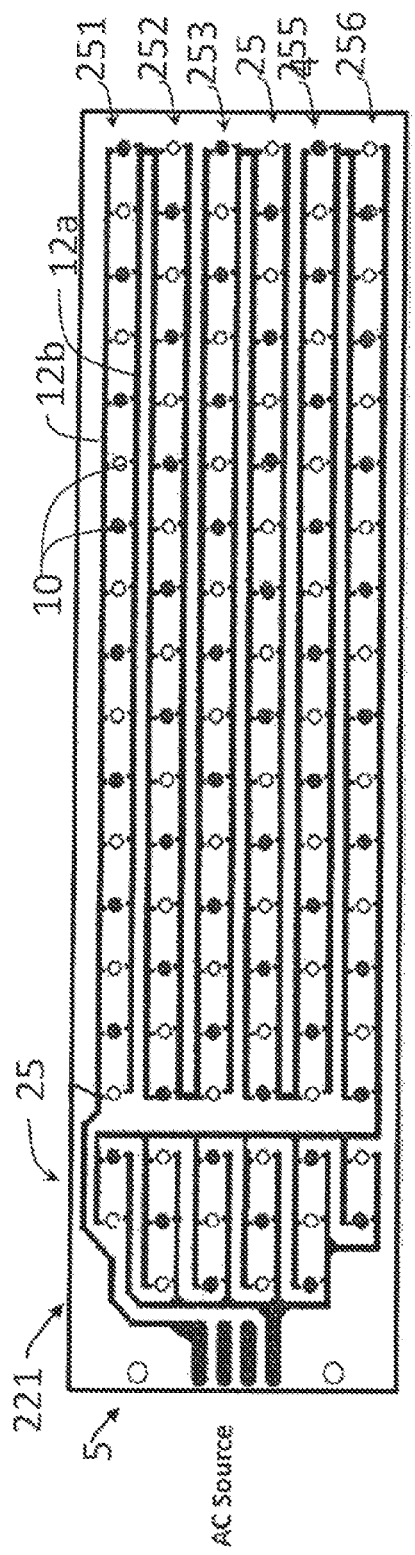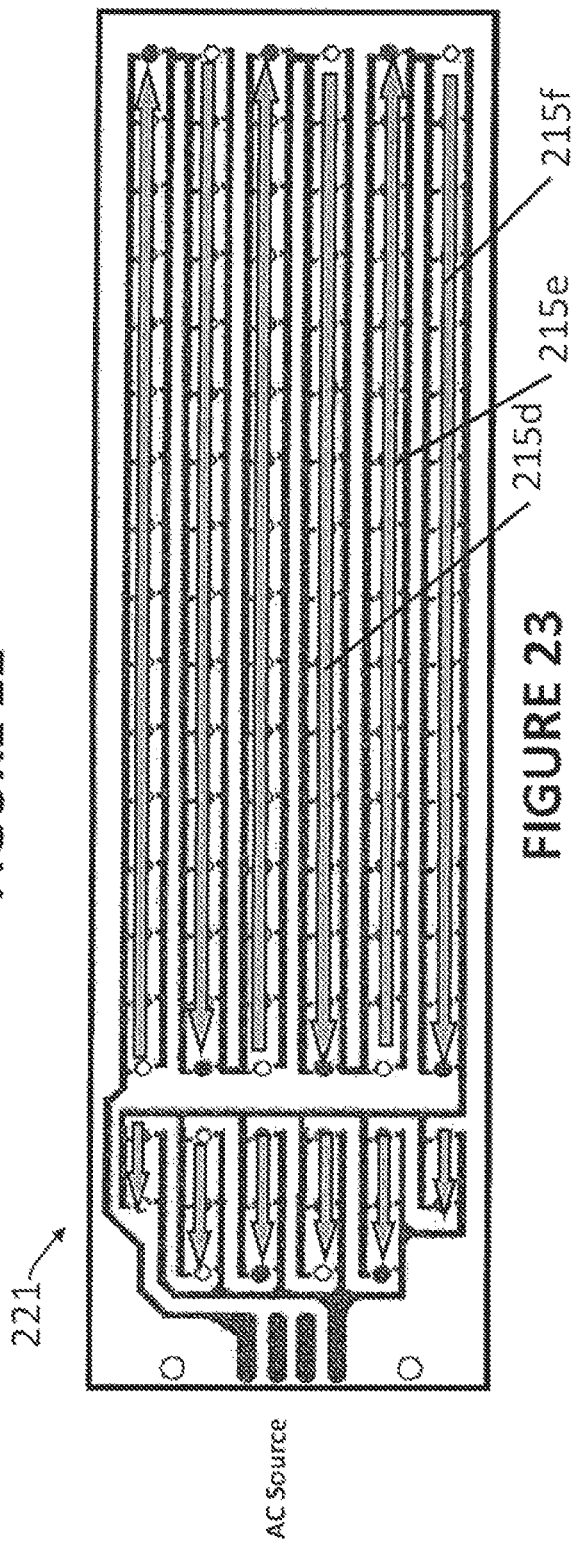

LIGHT AND BIOELECTRIC THERAPY PAD

CROSS-REFERENCE TO RELATED APPLICATION

This application claims the benefit of U.S. Provisional Application No. 61/730,653, filed on Nov. 28, 2012, the disclosure of which is incorporated herein by reference.

FIELD OF THE INVENTION

The present invention relates to light- and bioelectric-emitting pads for therapeutic methods.

BACKGROUND OF THE INVENTION

Two modalities to enhance wound healing that have been disclosed in the art are low level light therapy (LLLT) and bioelectric therapy. Each of these modalities has individually shown value in accelerating the healing of wounds. Low level light therapy utilizes light in the 600 to 1000 nm wavelength band to stimulate the biological healing process. Bioelectric therapy provides a device in direct contact with a bodily fluid to drive a small, constant and direct current of 1 to 10 microamps in the conductive bodily fluids of the wound to similarly stimulate wound healing. A recent bioelectric stimulation article with references has been published by Dr. Andrew L. Blount et. al in the Journal of Burn Care Research 2012; volume 33; pages 354-357, the disclosure of which is incorporated by reference in its entirety. A bioelectric stimulation product for wound care currently on the market is the Procellera™ Wound Dressing by Vomaris Innovations (www.vomaris.com).

Weaknesses of bioelectric therapy are the requirement for contact by the component elements of the device with a conductive bodily fluid in the vicinity of the wound, and the minimal depth of therapeutic stimulation. Bioelectric stimulating devices are disclosed in U.S. Pat. Nos. 7,457,667, 7,662,176, 7,672,719, 7,813,806, and 7,904,147. These patent disclosures require contact of the biological fluid with the electrodes to complete a current path and enable DC current to flow between the positive and negative electrodes of the device. This presents numerous technical weaknesses, including the potential deleterious effects of temperature on the level of current, the potential build up higher impedance material on the electrodes that can affect the level of current, the discharge of the electrodes over time (they are batteries), and the effect of any changes in "wetting" of the electrodes that affects the level of current.

Weaknesses of low-level light therapy are a lack of electronic stimulation and the dependence on stimulating chromophores. Conventional light therapy devices typical have limited and/or poor control of the light dosage. The delivery of light to the wound site is typically cumbersome when using conventional light therapy devices in the form of wands, screens, helmets, etc. Examples of such light therapy pads are disclosed in US Publication 2007/0233208, U.S. Pat. No. 6,096,066, U.S. Pat. No. 6,290,713, and US Publication 2006/0173514), the disclosures of which are incorporated by reference in their entireties. These disclosed light therapy pads each suffer from one or more of the following: inadequate control of light dosage, impractical means of controlling potential heat buildup between the light therapy pad and the treated tissue; limited flexibility; lack of a smooth pad surface for contacting the skin; mis-shaped to match a specific anatomical site to achieve a specific therapeutic outcome; and lack of a simple and practical means of attaching the light pad to the desired anatomical site.

SUMMARY OF THE INVENTION

The present invention provides a bioelectric therapy pad device that employs a bioelectric therapy modality that does not require direct contact the bodily fluid to activate the bioelectric therapy, and can be placed on or above other bandages, clothing, or medical fabrics, and a method using the therapy pad device to deliver bioelectric therapy adjacent tissue.

The present invention provides a light therapy pad that employs light stimulation, and a method using the light therapy pad to deliver light stimulation to adjacent tissue.

The present invention also provides a light and bioelectric therapy pad that combines light stimulation and bioelectric stimulation simultaneously to adjacent tissue, and a method combines both a light therapeutic modality and a bioelectric therapy modality for the therapeutic treatment of adjacent tissue. The light therapy and bioelectric therapy modalities can be employed simultaneously, alternately, sequentially or in any other temporal pattern. The device does not require direct contact with the bodily fluid to activate the bioelectric therapy, and can be placed on or above other bandages, clothing, or medical fabrics.

The present invention provides a light and bioelectric therapy pad for providing light stimulation and bioelectric stimulation to adjacent bodily tissue, including: a) a pad substrate, b) an electrical tracing circuit comprising a plurality of parallel, spaced-apart approximate linear tracings (ALTs), wherein each ALT comprises a plurality of light emitting diodes (LEDs), and directs current flow in one direction along the ALT during the positive drive cycle of an alternating current (AC), and current flow in the opposite direction along the ALT during the negative drive cycle of the AC, and c) an AC source connected to the electrical tracing circuit.

The present invention also provides an approximate linear tracing (ALT) that directs current flow in one direction along the ALT during the positive drive cycle of an alternating current (AC), and current flow in the opposite direction along the ALT during the negative drive cycle of the AC, the ALT including a plurality of light emitting diodes (LEDs) arranged in a row having a first end and an opposite second end, the plurality of LEDs in the row being wired in parallel between a first header tracing and a second header tracing, the plurality of LEDs including a first group of one or more LEDs arranged in a first direction wherein an anode of the LEDs of the first group is wired to the first header tracing and a cathode of the LEDs of the first group is wired to the second header tracing, and a second group of one or more LEDs arranged in a second direction wherein a cathode of the LEDs of the second group is wired to the first header tracing and the anode of the LEDs of the second group is wired to the second header tracing, and further including a first current supply tracing connected to the first header tracing at the first end of the row of LEDs, and a second current supply tracing connected to the second header tracing at the opposite second end of the row of LEDs.

The present invention also provides an electrical circuit comprising a plurality of approximate linear tracings (ALTs) provided herein, wherein a pair of adjacent ALT directs respective current flows in first opposite directions during the positive drive cycle, and respective current flows in second opposite directions during the negative drive cycle.

The present invention also provides a method for light stimulation and bioelectric stimulation to adjacent bodily tissue, comprising the steps of: a) applying a light and bioelectric therapy pad described herein to a body portion of a patient, the plurality of ALT including a first ALT and an adjacent second ALT, b) energizing the AC current source, c) effecting current flow in the first ALT in a first direction during the positive drive cycle of the AC, and in a second direction, opposite the first direction, during the negative drive cycle of the AC, d) effecting current flow in the adjacent second ALT in the second direction during the positive drive cycle of the AC, and in the first direction during the negative drive cycle of the AC, and e) emitting light from a first group of the plurality of LEDs of the first ALT and of the second ALT during the positive drive cycle of the AC, and emitting light from a second group of the plurality of LEDs of the first ALT and of the second ALT during the negative drive cycle of the AC, wherein the current flows in opposite directions in the first ALT and adjacent second ALT during both the positive drive cycle and the negative drive cycle of the AC, and induces therapeutic eddy currents within the tissue of the body portion.

An aspect of the present invention is a means and method of controlling the intensity and duration of a light therapy dose.

Another aspect of the present invention is a means and method for electronic temperature feedback, to prevent excessive temperature rise at the surface of the therapy pad.

A further aspect of the present invention is the thermal design of the therapy pad.

Another aspect of the present invention is a mechanism and method for attaching the device to a body portion of the patient.

Still another aspect of the present invention is a device having a shape that corresponds, contours to, and/or registers with an anatomical site of the body to achieve a specific therapeutic outcome.

Yet another aspect of the present invention is the use of reverse mount LED to achieve ultimate thinness, smoothness, thermal management, and flexibility of the therapy pad.

BRIEF DESCRIPTION OF THE DRAWINGS

FIG. 8 illustrates the eddy currents generated by the light and bioelectric therapy device in the dermis when the AC-powered device is placed over the skin, during the positive drive cycle of the AC.

FIG. 10 illustrates the eddy currents generated by the light and bioelectric therapy device in the dermis when the AC-powered device is placed over the skin, during the positive drive cycle of the AC.

FIG. 15 shows the physical design of a typical reverse mount LED.

FIG. 16A is a graph showing the Arndt-Schultz Law of light therapy.

FIG. 16B is a graph showing bioelectric healing effect vs. current signal intensity (amplitude) in the tissue, as taught in the prior art.

FIG. 17 shows typical curve relating LED drive current to light output for a typical LED.

FIG. 19 shows a cross-section of the lower leg of a human.

FIG. 20 shows a light therapy pad including LEDs and an electrical tracing layout use in a tibia bone marrow treatment.

FIG. 21 shows cumulative net current flows through standard linear tracing and the rows of LEDs in the therapy pad of FIG. 20.

FIG. 22 shows a therapy pad including LEDs and an electrical tracing layout use in a cerebral cortex treatment.

FIG. 23 shows cumulative net current flows through the rows of LEDs in the therapy pad of FIG. 22.

DETAILED DESCRIPTION OF THE INVENTION

Figure 1:
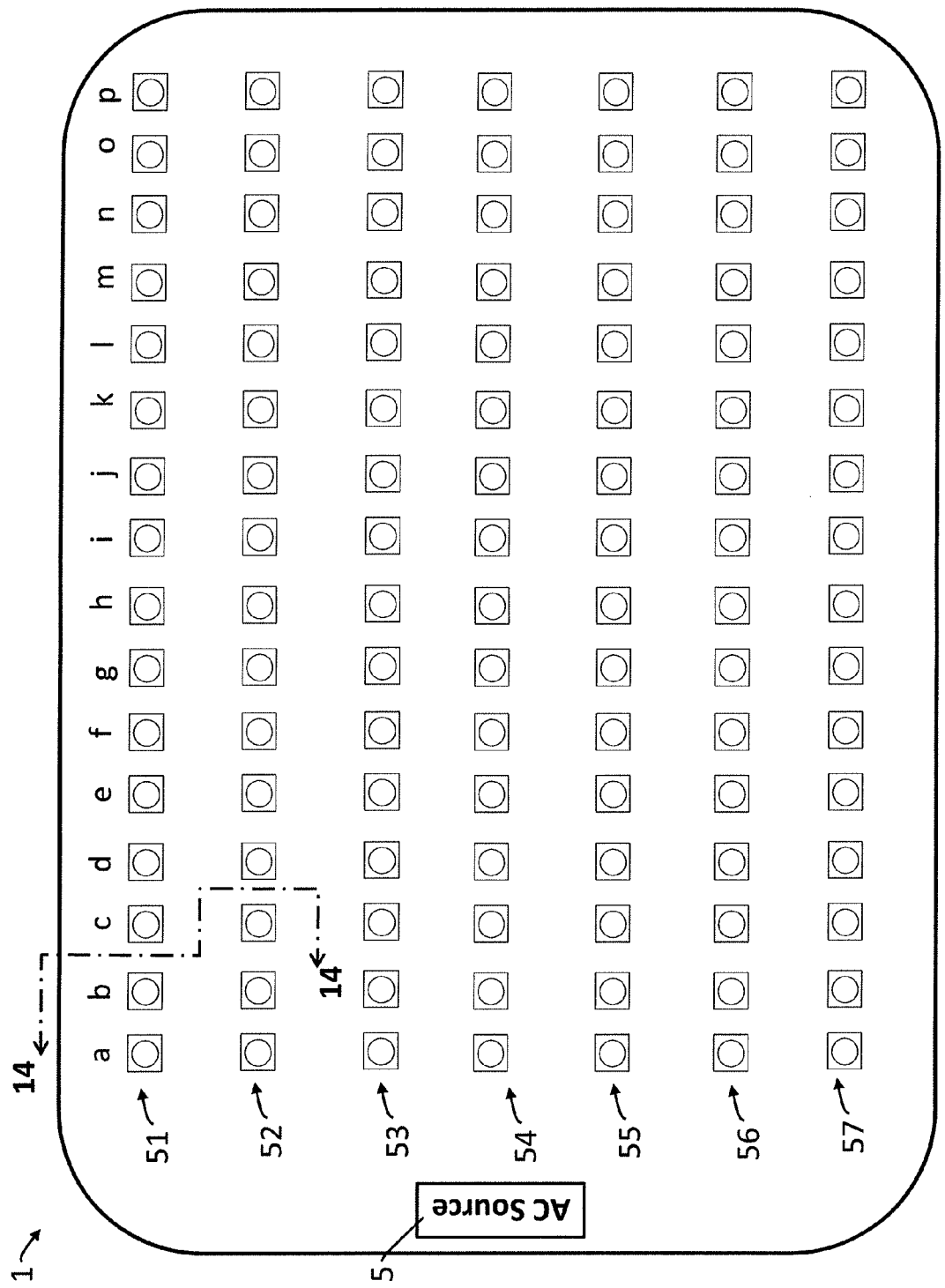
FIG. 1 shows a plan view of a light and bioelectric therapy device of the present invention.

The present invention employs independently, and in combination, the principles of unidirectional current flow in the forward direction through a diode, and Ampere's law of magnetic fields from current through a wire.

Current flows through a diode in the forward direction, from the anode terminal of the diode toward the cathode terminal of the diode. Current supplied at the anode terminal will flow through the diode. Current supplied at the cathode terminal will not flow through the diode.

The present invention provides a circuit comprising a plurality of diodes that are arranged and wired into an "approximate linear tracing" that provides a bioelectric therapy tracing. The plurality of diodes, typically light emitting diodes (LEDs), which also provide a source of light when current flows in the forward direction through the LED, are arranged in a row, and each LED in the row is wired in parallel with the other LEDs between a first header tracing and a second header tracing.

A first group of one or more LEDs from the plurality of LEDs is arranged in a first direction wherein the anode is wired to the first header tracing and the cathode is wired to the second header tracing. A second group of one or more LEDs (typically from the remaining plurality of LEDs) is arranged in a second direction wherein the cathode is wired to the first header tracing and the anode is wired to the second header tracing. A current flowing in a first direction from the first header tracing toward the second header tracing will flow through the first group of LEDs, but will not flow through the second group of LEDs. Conversely, a current flowing in a second direction from the second header tracing toward the first header tracing will flow through the second group of LEDs, but will not flow through the first group of LEDs. Using an alternating current (AC), the first group and second group of LEDs alternately allow current flow, and emit light, modulated at the frequency of the current change.

In a further aspect of the invention, the current flow in the first header tracing and the current flow in the second header tracing are co-directional, regardless of whether the current is flowing in the first direction from the first header tracing toward the second header tracing (during a positive drive cycle of the AC), or in the second direction from the second header tracing toward the first header tracing (during a negative drive cycle of the AC). To provide co-directional current flow in the first header tracing and the second header tracing, a first current supply connection to the first header tracing is made at a first end of the row of LEDs, typically before a first connection of the first header tracing to the first LEDs in the row of LEDs, and a second current supply connection to the second header tracing is made at an opposite second end of the row of LEDs, typically before a first connection of the second header tracing to the last LEDs in the row of LEDs.

The one or more LEDs of the first group and the one or more LEDs of the second group are distributed along the row. The distribution of the LEDs of the first group and second group can be random, or well distributed and even, or segregated into sub-groups. The number of LEDs in each of the first group and second group is typically about the same when LEDs of the same current rating are used. A different number of LEDs between the first group and second group of LEDs can be used, provided that the cumulative current capacity of the LEDs in each group are substantially the same, so as to not overload one or more LEDs in one of the groups when the current flows in that direction.

The result of the above features of two groups of LEDs wired in parallel and in opposite directions between a first header tracing and a second header tracing, with current supply connections to the first header tracing and second header tracing on opposite sides of the row of LEDs, is an approximate linear tracing having a substantially unidirectional flow of current. According to Ampere's law, a unidirectional flow of current in a tracing of a circuit creates a magnetic field around the tracing in a first direction when the alternating current flows in a first direction during the positive drive cycle of the AC, and a magnetic field around the tracing in the opposite second direction when the alternating current flows in the second direction during the negative drive cycle. The approximate linear tracing can be used as a bioelectric therapy tracing. Placing a plurality of these "approximate linear tracings" or bioelectric therapy tracings in a side-by-side, parallel pattern, can effect induced eddy currents within the body tissue when the AC-powered device is placed adjacent to the skin.

Figure 2:
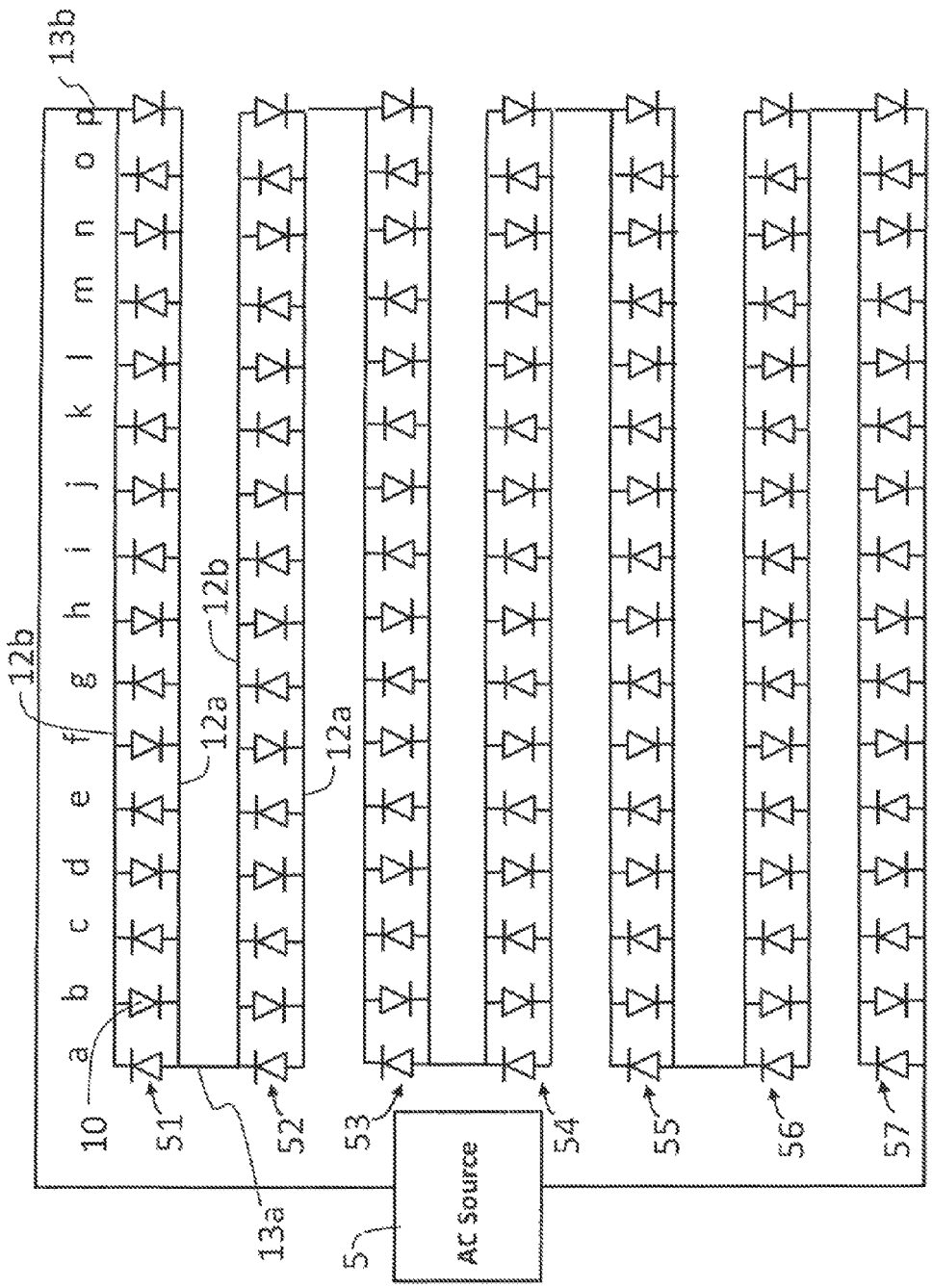
FIG. 2 shows a plan view of the electric circuit of the light and bioelectric therapy device.

FIG. 1 shows a light and bioelectric therapy pad that combines light therapy and bioelectric (induced current) therapy or stimulation. FIG. 2 shows a plurality of light emitting diodes (LEDs) 10 arranged within the therapy pad, and connected via electrical tracings to an alternating-current power source. Controllers (not shown) of well known type control the powering on-and-off of the alternating current to the circuit. The LEDs 10 are arranged in a matrix of a plurality of parallel rows of LEDs (rows 51, 52, 53, 54, 55, 56 and 57), with the LEDs in each row being positioned in parallel columns, namely a, b, c, d, e, f, g, h, i, j, k, l, m, n, o and p. Along each row, the LEDs 10 are sequenced in alternating orientation, one orientation being the LED with the anode (+ terminal) in electrical connection to a first header tracing 12a extending proximate and along one side of and parallel with the row of LEDs 10, and the cathode (– terminal) in electrical connection to a second header tracing 12b extending proximate and along the opposite side of and parallel with the row of LEDs 10.

Figure 3:
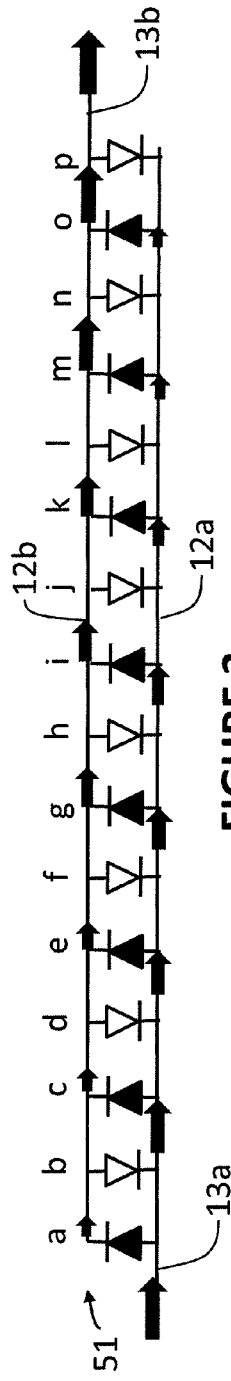
FIG. 3 shows an approximate linear tracing including a first group and a second group of LEDs, arranged in opposite directions, with a current flowing in a first direction through the approximate linear tracing during the positive drive cycle of an alternating current (AC).
Figure 4:
FIG. 4 shows the direction of the net effective linear current flow through the approximate linear tracing of LEDs of FIG. 3.

FIGS. 3 and 4 show current flow in a bioelectric tracing when the AC supply is in a positive drive cycle.

Each of first header tracing 12a and second header tracing 12b are connected to a respective current supply connection at opposite ends of the row of LEDs. First current supply connection 13a supplies current flow (shown by black arrows), during a positive drive cycle of the AC supply, to first header tracing 12a, providing directional current flow (left to right in FIG. 3) along first header tracing 12a. All wiring connections from the first header tracing, starting with the first LED 51a in the row of LEDs, run sequentially to the remaining LEDs in the row.

Second current supply connection 13b receives current flow (black arrows), during the same positive drive cycle of the AC supply, from second header tracing 12b, providing co-directional current flow (again, left to right in FIG. 3) along second header tracing 12b in the same direction as current flow in the first header tracing 12a. All wiring connections from the second header tracing again, ending with the last LED 51p in the row of LEDs, run sequentially from the row of LEDs.

During the positive drive cycle, current can only flow through an LED having an anode (+ terminal) connected to the first header tracing 12a, namely LEDs (by row and column) 51a, 51c, 51e, 51g, 51i, 51k, 51m, and 51o, depicted by black coloring of the diode. Current that flows out of these LEDs flows into second header tracing 12b.

Consequently, during a positive drive cycle of the AC supply, the net current flow 15 in the bioelectric tracing comprising the row 51 of LEDs is illustrated in FIG. 4, which is substantially from first current supply connection 13a to second current supply connection 13b (left to right).

Figure 5:
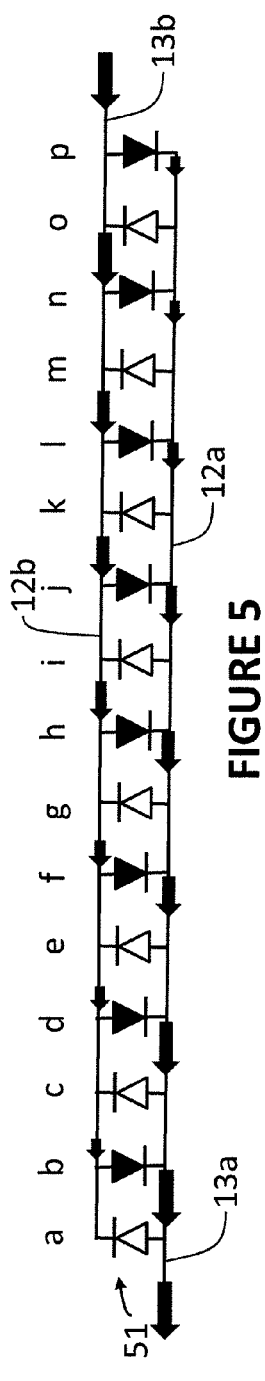
FIG. 5 shows the approximate linear tracing of FIG. 3 with the current flowing in an opposite second direction during the negative drive cycle of the AC.
Figure 6:
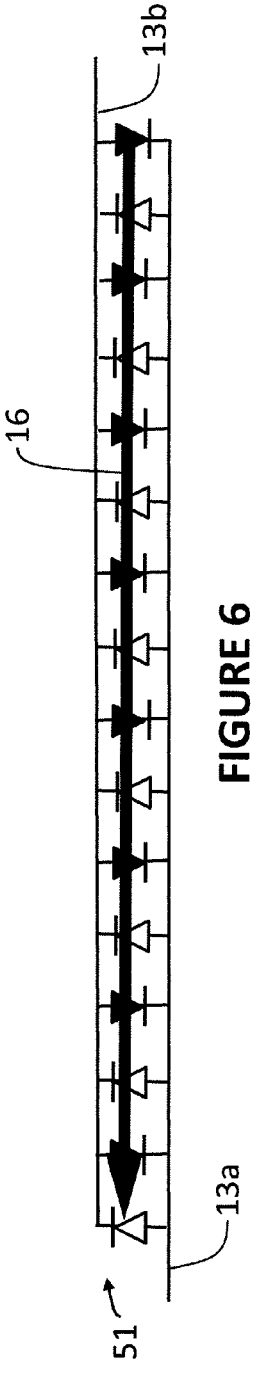
FIG. 6 shows the direction of the net effective linear current flow through the approximate linear tracing of LEDs of FIG. 5.

FIGS. 5 and 6 show current flow in the same bioelectric tracing when the AC supply is is a negative drive cycle.

During a negative drive cycle of the AC supply, second current supply connection 13b supplies current flow (shown by black arrows), to second header tracing 12b, providing directional current flow (right to left in FIG. 5) along second header tracing 12b. First current supply connection 13a receives current flow (black arrows), during the same negative drive cycle of the AC supply, from first header tracing 12a, providing co-directional current flow (again, right to left in FIG. 5) along first header tracing 12a in the same direction as current flow in the second header tracing 12b. During the negative drive cycle, current can only flow through an LED having an anode (+ terminal) connected to the second header tracing 12b, namely LEDs (by row and column) 51b, 51d, 51f, 51h, 51j, 51l, 51n, and 51p, depicted by black coloring of the diode. Current that flows out of these LEDs flows into first header tracing 12a.

Consequently, during a negative drive cycle of the AC supply, the net current flow 16 in the bioelectric tracing comprising the row 51 of LEDs is illustrated in FIG. 6, which is substantially from second current supply connection 13b to first current supply connection 13a (right to left).

Each row of LEDs in combination with the pair of header tracings 12a, 12b, and current supply connections connected on opposite ends of the row of LEDs to the respective header tracings, comprise an approximate linear tracing, with the net direction of current flow alternating with the positive and negative drive cycles of the AC supply.

Figure 7:
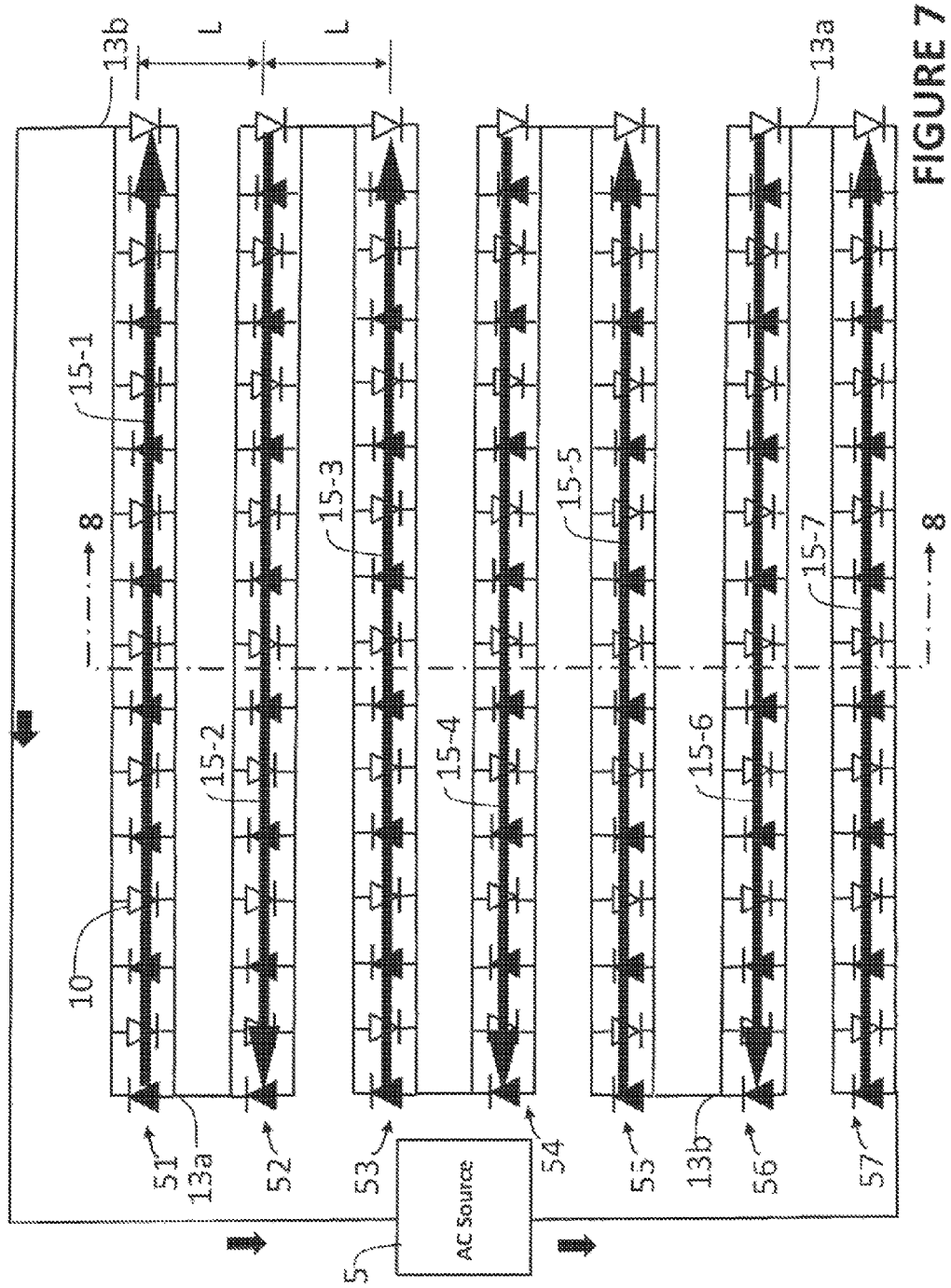
FIG. 7 shows the electric circuit of the light and bioelectric therapy device of FIG. 2, and the direction of the net effective linear current flowing through the plurality of parallel-arranged approximate linear tracings, during the positive drive cycle of the AC.

FIG. 7 shows during a positive drive cycle, the electrical wiring and LED circuit of FIG. 2, including the plurality of light emitting diodes (LEDs) 10 arranged in a plurality of parallel rows 51-57, illustrated as cumulative net current flows 15-1 through 15-7, wherein cumulative net current flows 15-1 is the current flow 15 through LED row 51, cumulative net current flows 15-2 is the current flow 15 through LED row 52, cumulative net current flows 15-3 is the current flow 15 through LED row 53, etc.

FIG. 8 illustrates, with the current flowing in the first direction through the device as shown in FIG. 7, the induced currents in the dermus resulting when the device is placed over the surface of the skin, as viewed along line 8-8 of FIG. 7. For LED rows 51, 53, 55 and 57, the cumulative net current flow 15-1, 15-3, 15-5 and 15-7 are "into the page" and are illustrated by a cross-lines "x" in the respective row, and which result in a clockwise-induce field 17 around each of LED rows 51, 53, 55 and 57. For LED rows 52, 54, and 56, the cumulative net current flow 15-2, 15-4, 15-6 and 15-8 are "out of the page" and are illustrated by a dot "•" in the respective row, and which result in a counter-clockwise-induce field 18 around each of LED rows 52, 54 and 56.

FIG. 8 also illustrates that the adjacent rows of clockwise-induced field 17 (e.g., row 51) and counter-clockwise-induce field 18 (e.g., row 52) results in oppositely-induced current flows 19a and 19b in the dermus below the respective LED rows 51-57.

Figure 9:
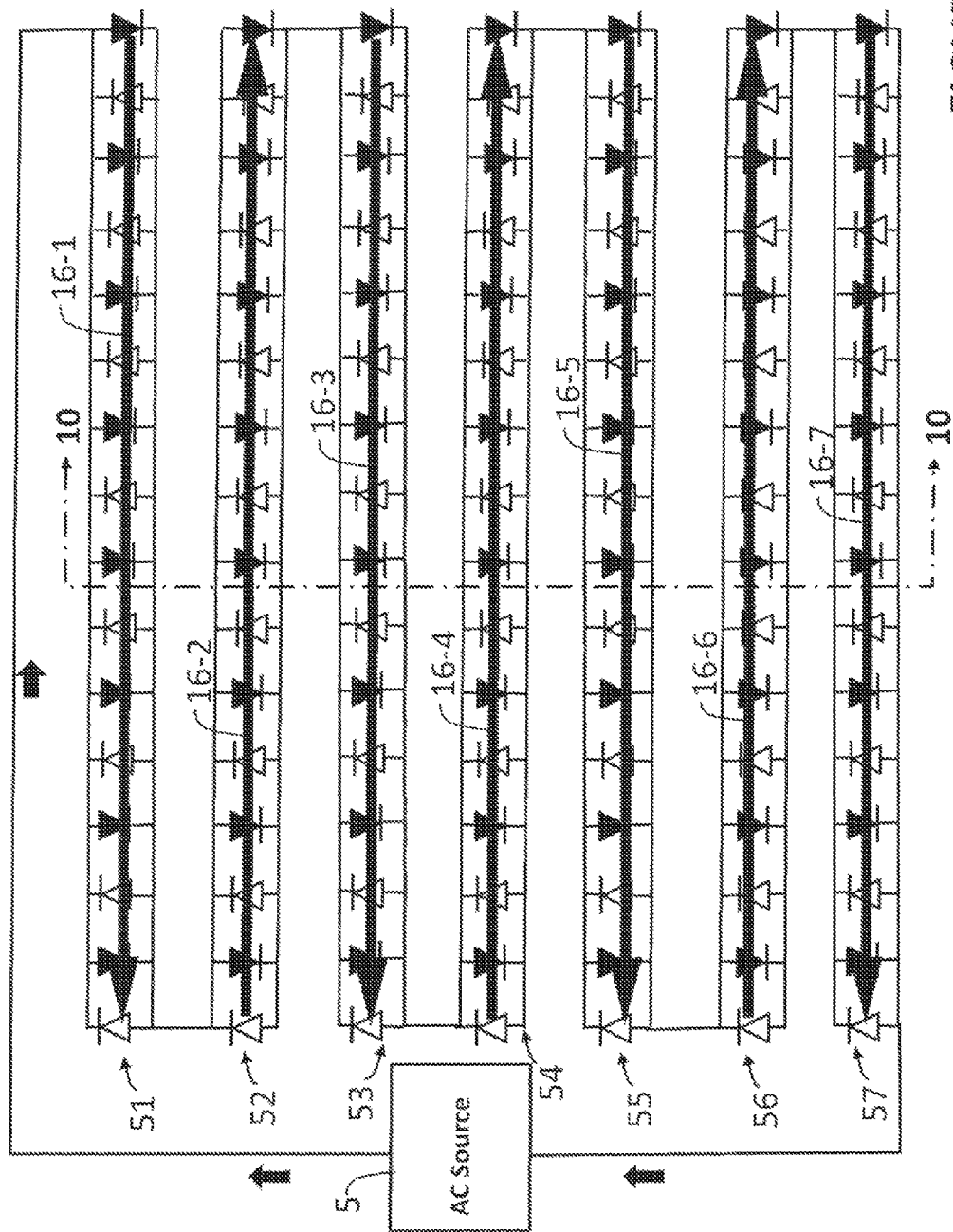
FIG. 9 shows the electric circuit of light and bioelectric therapy device of FIG. 2, and the opposite direction of the net effective linear current flows through the plurality of parallel-arranged approximate linear tracings, during the negative drive cycle of the AC.

Conversely, FIG. 9 shows the cumulative net current flows 16-1 through 16-7 during a negative drive cycle. FIG. 10 illustrates the induced clockwise fields 17 around each of LED rows 52, 54 and 56, and counter-clockwise fields 18 around each of LED rows 51, 53, 55 and 57, and the resulting oppositely-induced current flows 19a and 19b in the dermus below the respective LED rows 51-57.

Consequently, the alternating of current during the positive and negative drive cycles through the circuit of connecting wires and alternately-arranged LEDs, results in a corresponding alternating of induced current flows in the dermus below and in the vicinity of each LED row 51-57.

During the first half of the AC drive cycle (positive drive cycle), the half of the first group of LEDs in the illustrated rows of LEDs conduct current and illuminate, while during the second half of the AC drive cycle (negative drive cycle), the other half of the second group of LEDs conduct current and illuminate. A 50 Hz AC drive frequency results in a 100 Hz light emission frequency. The 100 Hz light therapy modulation frequency has been quoted in the literature as an advantageous light frequency for stimulating healing. The AC source can have a current output so as to provide a peak current output through an approximate linear tracing of at least about 0.3 ampere, and up to about 2 amp, and more typically of at least 0.6 ampere, or at least 0.7 ampere, or at least 0.8 ampere, or at least 0.9 ampere, or at least 1.0 ampere, and up to about 1.2 ampere, or up to about 1.1 ampere, or up to about 1.0 ampere, or up to about 0.9 ampere; such as about 1 amp.

When the light pad is laid directly on skin and is driven with an AC current of 0.8 A peak to peak at a frequency of 50 Hz, the induced tissue eddy current is determined to be about 5 microampere. This induced current magnitude is well within effective therapeutic current levels given in the literature, typically about 0.1 to about 250 microamperes, and more typically between about 1 and 50 microamperes, as illustrated in FIG. 16B. FIG. 16B shows FIG. 3 of U.S. Pat. No. 7,117,034 issued to Kronberg, the disclosure of which is incorporated by reference in its entirety), illustrating a level of therapeutic benefit delivered by current density (amplitude) with the peak therapeutic effectiveness falling within the current density of about one to ten microamperes per square centimeter. The calculation of the magnitude of the induced eddy currents 17 and 18 within the dermis tissue follows. The properties of the dermis tissue are estimated using blood, which is the component with the lowest resistivity (highest conductivity) in the body tissue.

Calculation of Peak Tissue Current Induced by Light Therapy Pad

Resistivity of blood=1.7 Ωm (source: various technical sources)

Permeability of the human body: $\mu_r=1=\mu_0=1.5\times10^{-6}$ Tm/A (where T is Tesla)

Length (L) and area (A) of tissue resistor based on the light pad trace geometry:

L=0.01 m (spacing of traces "L" shown in FIG. 8)

A=0.005 m wide (along a rows of LEDs)×0.005 m deep (depth "d" into the tissue as shown in FIG. 8)=0.000025 m². (This area is similar to that of the battery cells of a Procellera® bioelectric wound dressing, described herein above.)

Electrical resistance of blood (R) within this defined space=Resistivity×Length/Area=1.7 Ωm×0.01 m/0.000025 m²=680Ω.

Induced tissue Eddy current $$(i) = \frac{\frac{d\phi}{dt}}{R}$$

where dØ=magnetic flux, dt=0.02 sec (50 Hz), and R=680Ω. (Eddy current equation from physics text book). Magnetic flux (dØ) for parallel straight wires (the condition within the light pad traces) =

$$\frac{\mu_r dI}{2\pi r}$$ (equation from physics text book), where r is at a distance of 0.005 m (depth into tissue).

Therefore, $$d\emptyset = \left(1.25 \times \frac{10^{-6} \text{Tm}}{\text{A}} \times 0.8 \text{ A} \times 2\right) / 0.005 \text{ m} \times 2\pi = 64 \times 10^{-6} \text{T}$$

(The "times 2" accounts for the two parallel rows of LEDs in the light pad, acting as conductors with currents flowing in the opposite direction resulting in constructive magnetic flux as in the case of a coil; for example, row 51 and 52 in FIG. 7).

The changing magnetic flux=$d\emptyset/dt$=$64 \times 10^{-6}$ T/0.02 sec=$3200 \times 10^{-6}$ T/sec.

Induced tissue Eddy current=$3200 \times 10^{-6}$ T/sec÷680Ω~5 µA.

The device of the present invention does not require direct contact with the biological fluid of the wound. The AC current is induced in the adjacent tissue through the conductivity of blood and the changing magnetic flux generated by the AC current in the pad.

From the standpoint of the bioelectric therapy modality the rows of LEDs function as approximate linear tracings. An aspect of the present invention is the inclusion of one or more standard linear tracings in combination with the one or more approximate linear tracings to provide bioelectric therapy in combination with photo therapy. The spacing between the adjacent tracings, whether standard linear tracings or approximate linear tracings, can be at least about 4 mm, and up to about 14 mm, and more typically at least about 5 mm, or at least about 8 mm, and up to about 12 mm, such as 10 mm.

Figure 11:
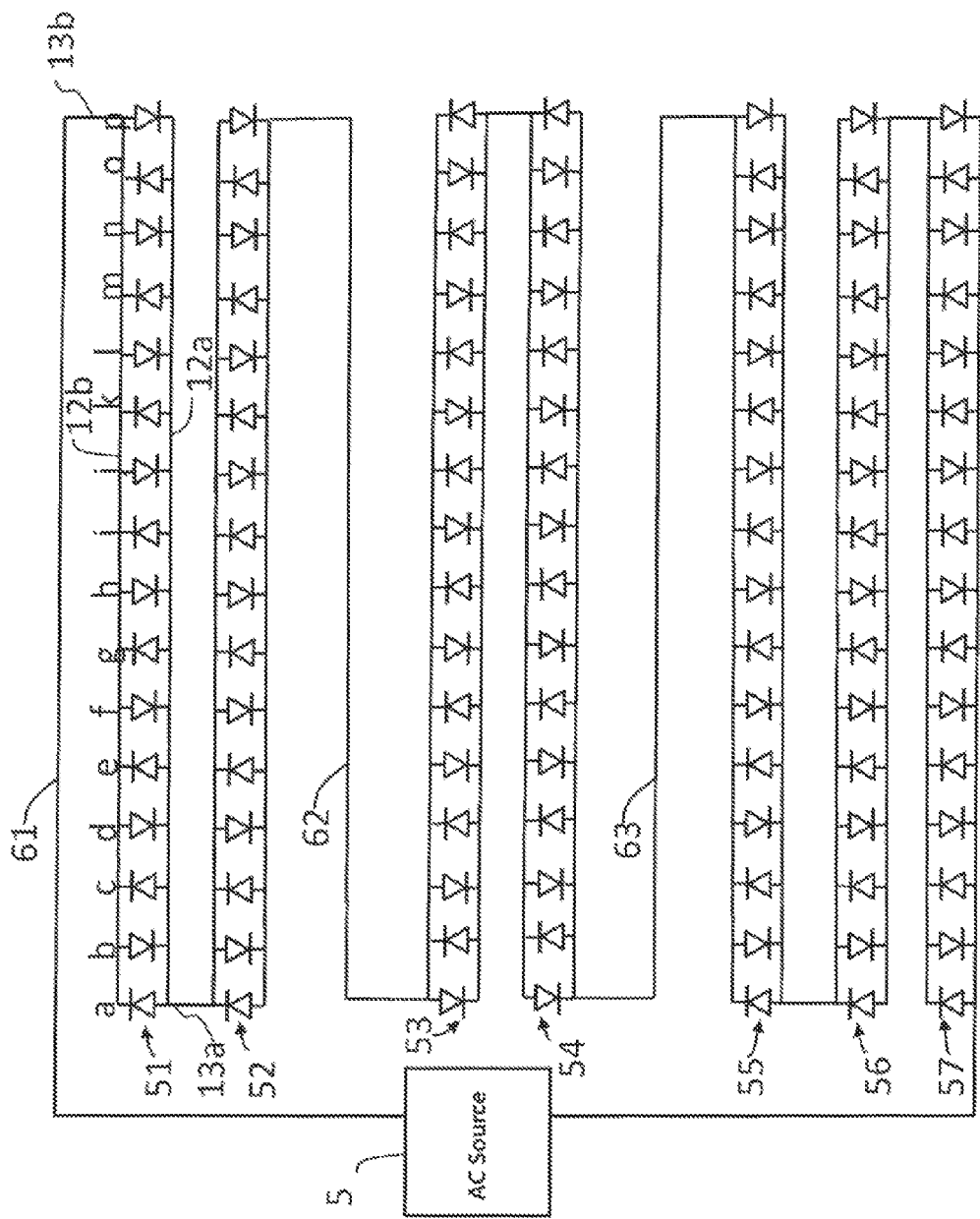
FIG. 11 shows an alternative electric tracing of the light and bioelectric therapy device that includes one or more standard linear tracings.

FIG. 11 shows an example of a bioelectric and photo therapy device in which one or more standard linear tracings are wired in series with the one or more approximate linear tracings to provide a pattern of parallel, spaced-apart linear tracings. In the illustrated embodiment, from the top of the figure working down, the first linear tracing is a standard linear tracing wire 61 which is aligned parallel with the row 51 of LEDs, and connects the array of LEDs to the AC source 5. The second and third linear tracings are the ALTs of rows 51 and 52 of LEDs. The fourth linear tracing is another standard linear tracing of wire 62 which connects the ALT of row 52 of LEDs with the ALT of row 53 of LEDs. The fifth and sixth linear tracings are the ALTs of rows 53 and 54 of LEDs. The seventh linear tracing is another standard linear tracing of wire 63 which connects the ALT of row 54 of LEDs with the ALT of row 55 of LEDs. And the eighth, ninth, and tenth linear tracings are the ALTs of rows 55, 56 and 57 of LEDs.

Figure 12:
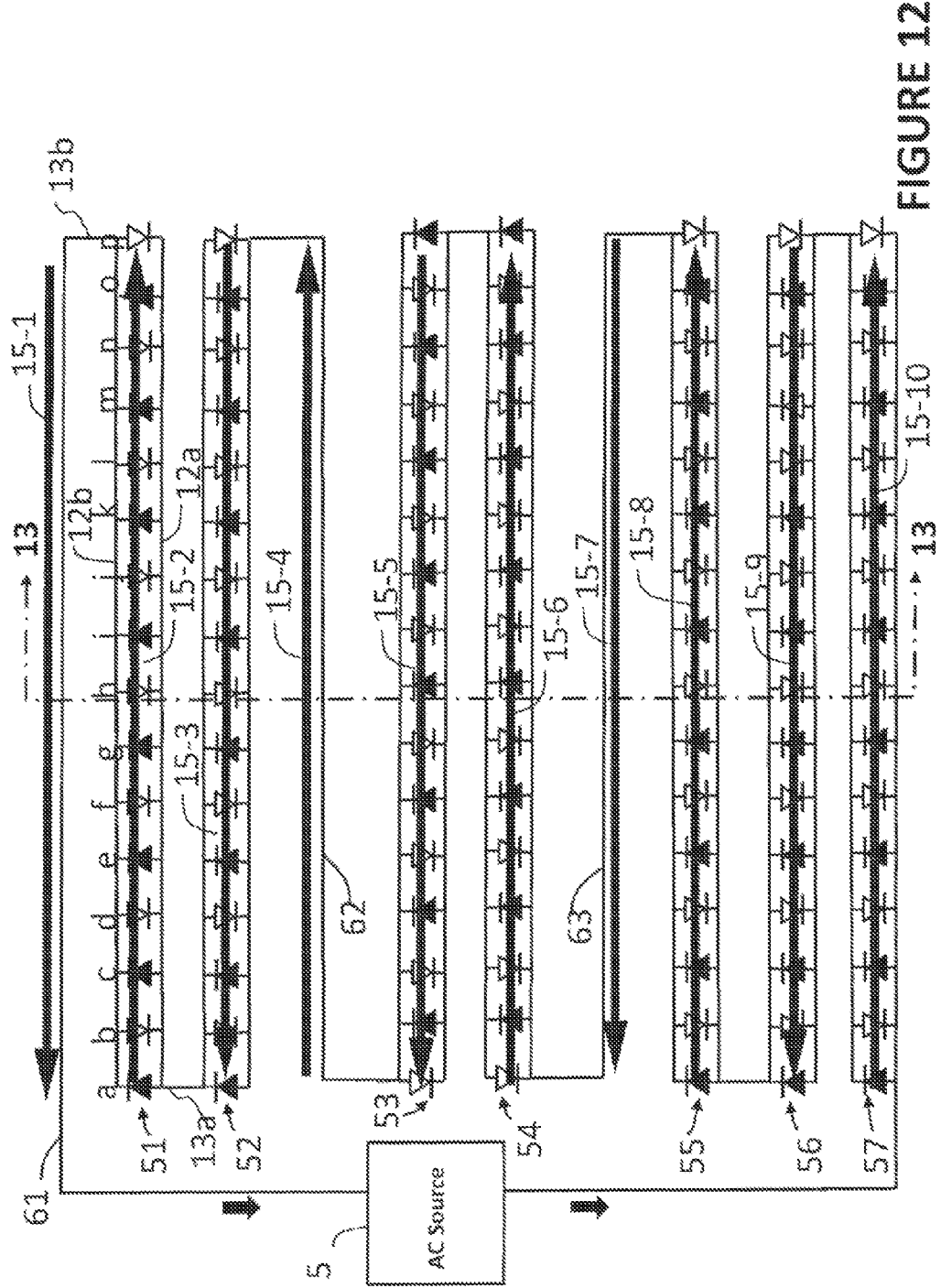
FIG. 12 shows the electric circuit of FIG. 11, and the direction of the net effective linear current flows through the plurality of parallel-arranged approximate linear tracings of LEDs and the standard linear tracings, during the positive drive cycle of the AC.

FIG. 12 shows during a positive drive cycle of AC source 5, the electrical wiring and LED circuit of FIG. 11, including the plurality of light emitting diodes (LEDs) 10 arranged in a plurality of parallel ALTs of rows of LEDs 51-57 and the intermediate standard linear tracings of wiring 61, 62 and 63, illustrated as ten cumulative net current flows 15-1 through 15-10, wherein cumulative net current flow 15-1 is the current flow 15 through standard linear tracing 61, cumulative net current flow 15-2 and 15-3 are the current flows 15 through LED rows 51 and 52, cumulative net current flow 15-4 is the current flow 15 through standard linear tracing 62, cumulative net current flows 15-5 and 15-6 are the current flows 15 through LED rows 53 and 54, cumulative net current flow 15-7 is the current flow 15 through standard linear tracing 63, and the cumulative net current flows 15-8, 15-9 and 15-10 are the current flows 15 through LED rows 55, 56 and 57.

Figure 13:
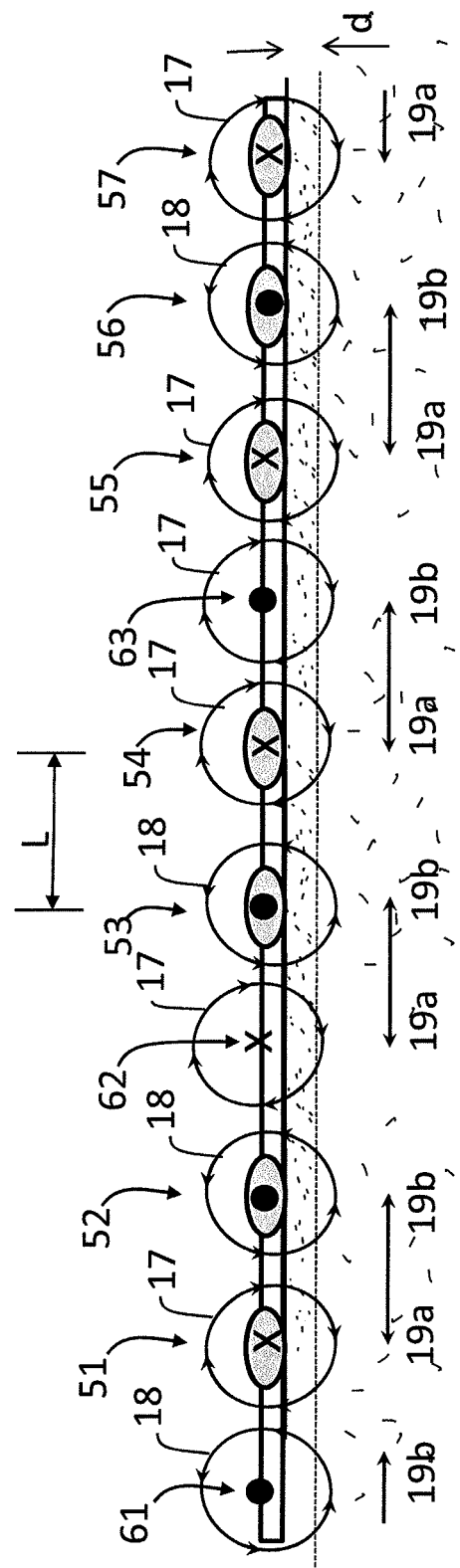
FIG. 13 illustrates the eddy currents generated by the combination light-induced field therapy device in the dermis when the AC-powered device of FIG. 12 is placed over the skin, during the positive drive cycle of the AC.

FIG. 13 illustrates, with the current flowing in the positive drive cycle of AC source 5 as shown in FIG. 12, the induced currents in the dermis resulting when the device is placed over the surface of the skin, as viewed along line 13-13 of FIG. 12. For the ALTs of LED rows 51, 54, 55 and 57, and standard linear tracing of wiring 62, the cumulative net current flow 15-2, 15-4, 15-6, 15-8 and 15-10 are "into the page" and are illustrated by a cross-lines "x" in the respective row, and which result in a clockwise-induce field 17 around each of LED rows 51, 54, 55 and 57 and standard linear tracing wiring 62. For ALTs of LED rows 52, 54, and 56, and standard linear tracing of wirings 61 and 63, the cumulative net current flow 15-1, 15-3, 15-5, 15-7 and 15-9 are "out of the page" and are illustrated by a dot "•" in the respective row, and which result in a counter-clockwise-induce field 18 around each of LED rows 52, 54 and 56 and standard linear tracing of wirings 61 and 63.

FIG. 13 also illustrates that the adjacent rows of clockwise-induced field 17 (e.g., row 51) and counter-clockwise-induce field 18 (e.g., row 52) results in oppositely-induced current flows 19a and 19b in the dermus below the respective LED rows 51-57, as well as the standard linear tracings wiring 61-63.

It can be understood that any variation of rows of LEDs in approximate linear tracings (ALTs) and standard linear wiring runs (standard linear tracing) can be used to achieve the desired bioelectric therapy effect. For example, a row of LEDs (approximate linear tracing) can alternate with a standard wiring run (standard linear tracing); or a plurality of row of LEDs (approximate linear tracings) can be laid, followed by a plurality of row of standard wiring run (standard linear tracing), and any combination therebetween. Pads having combinations of approximate linear tracings and standard linear tracings can be developed and designed for specific therapeutic requirements, depending upon the bioelectric therapy and phototherapeutic requirements.

Figure 14:
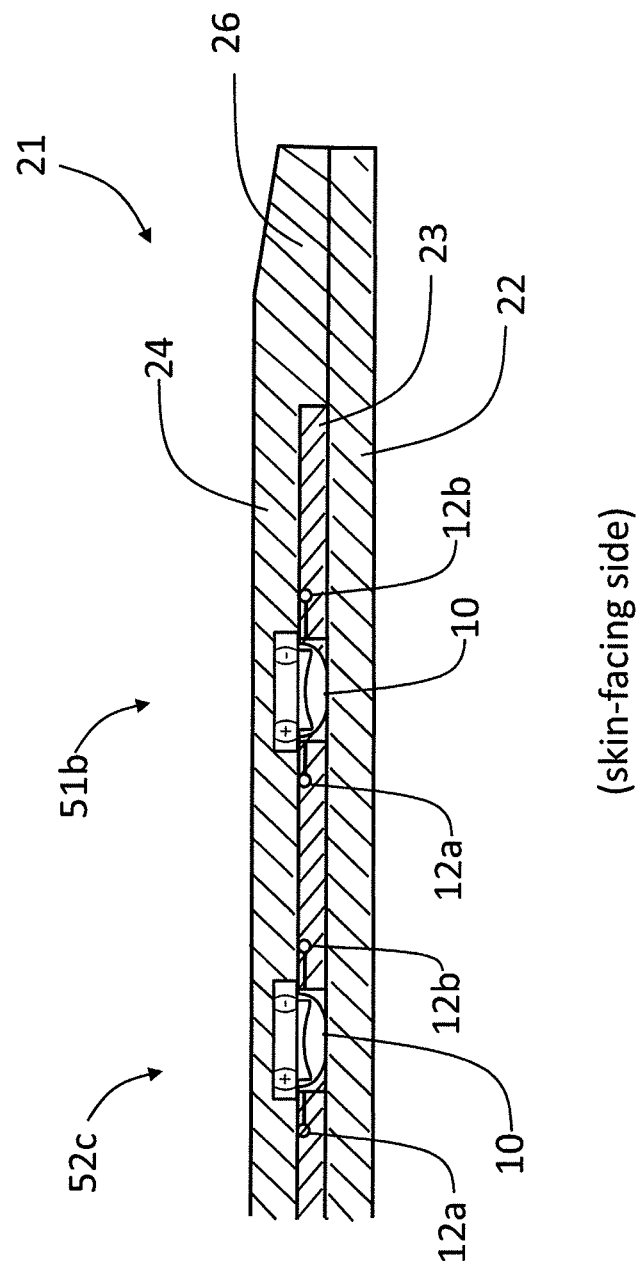
FIG. 14 shows general construction of the therapy pad of the invention, viewed through line 14-14 of the light and bioelectric therapy device of FIG. 1.

The general construction of the light therapy pad is illustrated in FIG. 14, which is a partial cross-sectional view of the therapy pad shown in FIG. 1. The light therapy pad structure 21 is constructed of a skin-facing layer of material 22, typically in the form of a film, a substrate 23 for carrying the light sources and electrical tracings, typically in the form of a flexible substrate layer, and an outer, heat dissipating layer 24, typically in the form of a film.

The skin-facing layer 22 can include a transparent, thermally insulative layer that permits light transmission. A non-limiting example of a skin-facing layer is clear silicone sheeting is McMaster Carr part #86915K, available in various sheet thicknesses, from about 10 to about 80 mil (0.25-2.0 mm), and for example, clear silicone sheeting having a thickness of about 0.20±0.10 mil (0.50±0.25 mm) as MC #86915K14. The thickness of the skin-facing layer 22 is typically 0.5 mm to about 5 mm, more typically about 1.0 mm, and has a durometer (flexibility/softness) of about 100 A or less, more typically about 40 A durometer or less. The clear silicone cover layer results in a smooth, flat, non-irritating skin-interface surface.

The flexible substrate 23 provides a circuit board that carries the LED light sources, illustrated as reverse-mounted LEDS, along with the electrical traces and power and control circuitry. The circuit board substrate 23 is an ultra-thin (for example, 0.13 mm thick) polyimide film with single side traces. Reverse-mounted LEDs 10 are mounted to the substrate 23 from the back, through holes 25 (for example, 2.0 mm diameter) in the substrate. The physical design of a typical reverse mount LED made by Osram is shown in FIG. 15, which shows that the thickness of the LED referenced to the back surface of the circuit board substrate (the solder surface of the LED) is typically 0.5 mm. In the illustrated embodiment, subtracting the thickness of the flex board plus the thickness of the solder pad (0.06 mm), the LED can protrude through the hole 25 and beyond the front surface of the circuit board substrate 23 by a minimal distance, for example about 0.3 mm (0.012"), which is well within the thickness tolerance of the skin-facing layer 22.

The light sources can include non-coherent light emitters (LEDs), or coherent light emitting laser diodes. The light sources are typically light emitting diodes (LEDs) having a principal emission wavelength in the range of 350 nm through 1,000 nm. Different wavelength bands can be selected, to produce different therapeutic effects. The LEDs can be packaged in the reverse mount design.

The heat dissipating layer 24 is preferably optimized to conduct the pad's internal heat, generated by the powering of the light sources, to the back surface (opposite the skin-facing side). The heat dissipating layer can comprise a thermally conductive, and preferably electrically insulating, material that is in thermal-transfer contact with the back sides of the LEDs 10, the flexible substrate 23, and the skin-facing layer 22. A non-limiting example of a heat dissipating layer is a thermally-conductive, optically-opaque silicone layer, for example, Stockwell Elastomerics TC1000 which has a thermal conductivity of 1.3 W/mK.

In addition, the pad includes an optically opaque outer layer of that extends beyond the edge of the light-generating LEDs, typically by at least 2 cm, and optionally around the edges of the pad, to contain (block) effectively all light given off by the light pad from passing out the sides of the light pad. The heat dissipating layer 24 can also be optically opaque. In an alternative embodiment, the optically opaque outer layer (for example, the optically-opaque heat dissipating layer 24) can extend beyond the edge of both the flexible substrate 23, and the skin-facing layer 22, to further minimize the escape of light out the side edges of the light pad.

The light therapy pad structure 21 is configured to have a smooth, continuous surface, and is preferably devoid of any ventilation slots or apertures, as are taught in various prior art light therapy pads to provide vapor channels, and of any fins or other cooling features to aid dissipation of heat. Slots, apertures or semi-permeable membranes in a pad can provide a haven for bacteria growth and are difficult to clean and disinfect. The present invention provides a smooth skin-facing surface and smooth back surface that are flexible.

The overall minimal thickness of the light pad structure 21, typically between about 2 mm to 5 mm, and in typical embodiment about 2.6 mm, provides maximum flexibility and minimal weight (about 50 gm). All these features— smoothness, flexibility, and weight—can create a user-friendly and positive user experience. Many medical conditions such as wounds, burns, rashes, acne, and peripheral neuropathy can especially benefit from these features.

The present invention provides a light therapy pad and electronic control system that can monitor the electrical current to the light sources of the light therapy pad, and determine when a desired light therapy dose has been satisfied. It can monitor the temperature at the skin/pad interface with a temperature sensor located within or on the light therapy pad structure, which is interfaced to the light pad electronic control, to allow maximum LED drive current while maintaining a desirable and safe pad/skin interface temperature, through closed loop control of the LED drive current. The structure of the light therapy pad includes layers of material that optimize the conduction of internal heat to the back surface of the pad (opposite the skin-facing surface), and can include a transparent silicone skin-facing layer, and a thermally conductive (but electrically insulating) layer on the back side of the LED flex circuit. The use of reverse mount LEDs also supports conduction of excess heat to the back side of the pad, while achieving minimal pad thickness, maximum pad flexibility, a smooth skin/pad interface surface, and light weight. These features are especially important when treating nerve sensitivity conditions such as peripheral neuropathy where any physical irritation of the skin surface is amplified by the patient's hypersensitive nerve endings. The light therapy pad also can incorporate a fast and secure means of attaching the light pad to the body surface, and can include pad structure shapes (the footprint or plan view pattern) that correspond to a specific anatomical site to achieve a specific therapeutic outcome.

Light Dose Determination and Control

A demonstration of the importance of light therapy dose is illustrated in the Arndt-Schultz Law graph show as FIG. 16. An electronic control system of the light therapy pad of the present invention provides a means for delivering a therapeutically-effective total light dosage that can be pre-determined and controlled. LEDs exhibit a predictable light intensity output as a function of drive current when operated at a known temperature.

An example LED of the current invention is the Osram "LS P47F-U1AA-1-1". This LED is a reverse mount design with a peak output wavelength of 645 nm. The typical efficiency of conversion of electrical drive power (in watts) to optical light power (in watts) is 30% for this LED when operating at a temperature of 35° C. A typical desirable light therapy dose is 2.0 J/cm$^2$ within the treated tissue. FIG. 17 shows a typical curve relating LED drive current to light output for a typical LED. This curve shows the linear relationship between drive current and light output within the operating temperature range of the LED.

Figure 18:
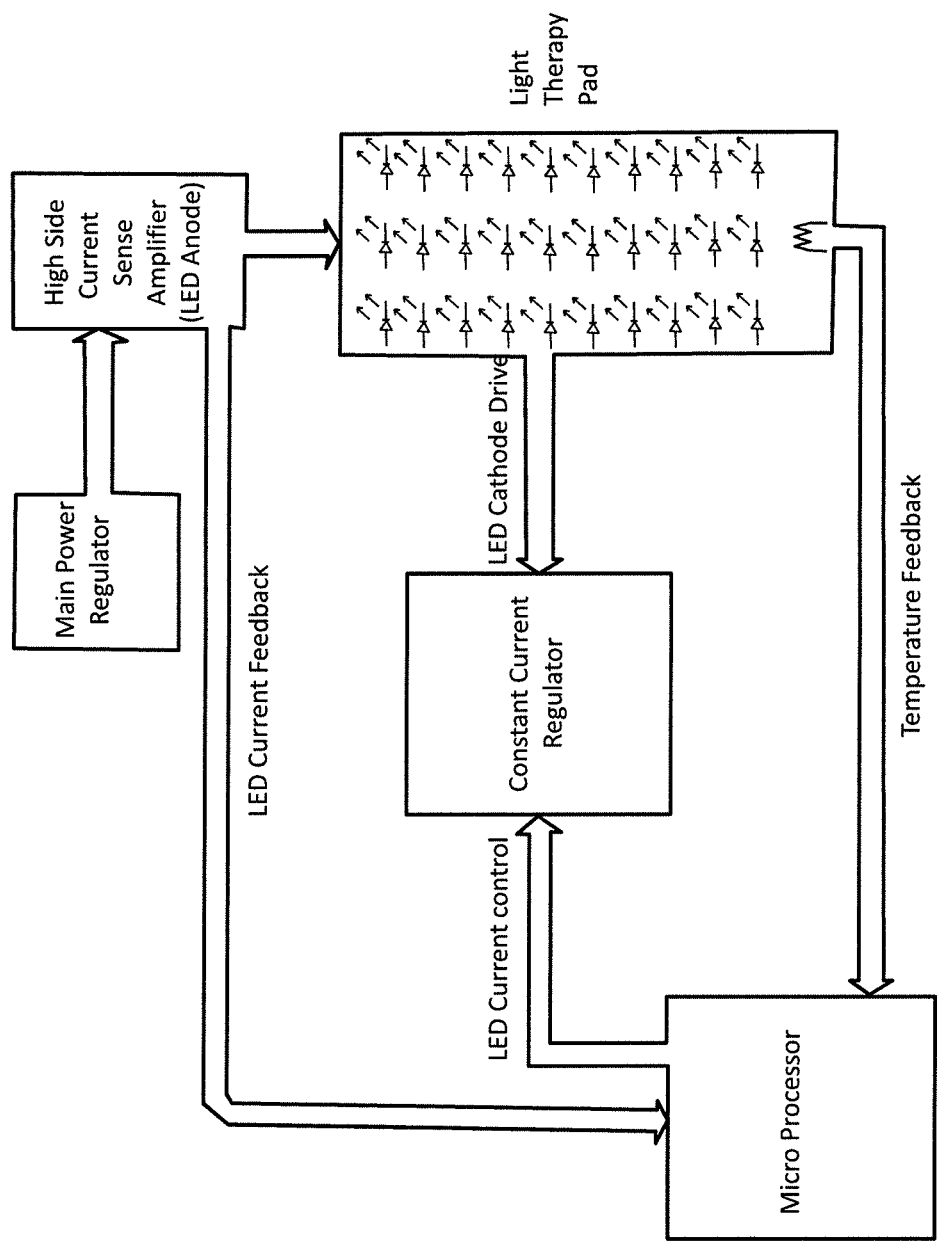
FIG. 18 shows a block diagram of an electronic controller for controlling LEDs, a thermistor, and the electrical tracings of the light therapy pad.

An electronic controller is located within a separate enclosure and is attached electronically to the LEDs, a thermistor, and the electrical tracings of the light therapy pad with a 4-conductor cable. In a typical embodiment, the four conductors are identified as: LED Anode, LED Cathode, Thermistor+, and Thermistor−. A block diagram of the electronic controller is shown as FIG. 18.

The thermistor output information is used by the microprocessor to control the current to the LEDS of the light therapy pad through a closed loop arrangement, which is commonly known. If the temperature is significantly below the target temperature (for example, 35° C.) the microprocessor sends maximum drive current through the tracings and to the LEDs of the light therapy pad. As the temperature of the light therapy pad structure warms and approaches 35° C., the microprocessor reduces the drive current through the tracings and to the LEDs in the closed loop arrangement. The microprocessor drives the LEDs with sufficient current to constantly maintain a desired target or target range of temperature. The electronic controller can include a Current Sense Amplifier that provides current data to the microprocessor. This current data is used to determine and control the end point of the therapy as described herein after, to deliver a controlled and known dose of light therapy. The firmware programmed into the microprocessor to perform these functions is well known in the art.

The power to the electronic controller can be provided with a rechargeable battery pack or a common AC/DC wall mount adapter of the proper voltage and current rating, as are also commonly known in the art.

In the determination of a correct total dosage of light, a determination can be made of the amount or portion of the total emitted light that penetrates into the target tissue. This determination includes knowledge of or a measure of the tissue optical properties. The target tissue in the body can include, for example, the marrow of a bone. For example, measurements of light intensity were performed within the tibia bone marrow when illuminated from outside the skin, and it was found that for the adult Caucasian male, 24% of the incident light power at 645 nm is measured within the marrow of the tibia when illuminated on the flat anterior surface of the tibia.

The total dosage of light for a particular therapeutic light treatment can range from at least about 0.5 J/cm², and up to about 10 J/cm², more typically from at least about 1 J/cm², and up to about 5 J/cm².

An example calculation of the total LED current corresponding to a 2.0 J/cm² dose within this bone marrow of the tibia follows:

Target light therapy dose within the tibia bone marrow: 2.0 J/cm²

Required light dose launched from light therapy pad, assuming 24% transmission to marrow: 8.3 J/cm²

Light power output of pad at 30 ma drive current/LED: 7.0 mW/cm²

Time required to achieve 8.3 J/cm² from the light pad: 20 minutes

Electrical power achieving 6.3 J/cm² light power in a 160 cm² area pad: 3.7 watts Drive Current required for light pad operating at 10 Vdc: 370 ma Total current to deliver desired dose of light therapy: 440 coulombs The drive current to the light therapy pad in the present invention, when used in a light therapy mode, is a variable determined by the temperature of or at the light therapy pad/skin interface. The current can be adjusted to maintain a comfortable 35° C. light therapy pad/skin interface temperature. Therefore the initial drive current will be higher and will decrease as the temperature rises. The delivery of the desired light therapy dose is achieved by integrating the area under the drive current vs. time curve. For the example given, when this area (coulombs) equals 440, the light dose has been delivered and the light therapy pad is turned off. The electronic control unit performs the measurement of coulombs as well as maintains the desired temperature. Since temperature is a variable affecting the electrical to light conversion efficiency of the LED, the determination and control of the temperature aids achieving high accuracy in the light dose calculation.

To achieve an effective minimum light energy and to minimize treatment time, it is preferred to maximize the drive current to the light therapy pad while minimizing heat buildup (temperature increase) at the pad/skin interface. The light therapy pad structure typically includes a thermally-insulating clear silicone layer between the LEDs and the skin, to minimize conductive heat toward the skin, and a thermally conductive silicone layer on the outside surface of the LEDs and substrate, to draw heat away from the light pad toward the back surface, to optimize convective and radiant cooling of the light therapy pad. The use of reverse-mount LEDs places the circuit board heat sinks (i.e., traces and LED solder pads) on the back side of the circuit board away from the skin surface, and into contact with the heat-conductive silicone layer. This design optimizes the removal of excess light pad heat from the light pad/skin interface and enables maximum LED drive current by minimizing heat build up at the skin/pad interface.

When the light therapy mode is used in combination with the bioelectric stimulation mode, the LEDs are powered using AC drive current, which induce the therapeutic eddy currents within the tissue as described herein before. The use of AC drive current results in a 50% duty cycle, modulated light output, and allows peak light intensity and minimal heat generation.

Anatomically Appropriate Light Pad Shapes

The present invention provides a therapy pad that can be constructed in a wide variety of shapes (that is, the footprint of the pad) to correspond to, contours to, and/or register with an anatomical site of the body to achieve a specific therapeutic outcome. Non-limiting examples of anatomical site of the body to which the therapy pad can correspond to, contours to, and/or register, including the shin bone (tibia), the forehead, and the forearm. Recent research shows the beneficial effects of administering light therapy to the stem cells for treatment of infarcts, trauma, other systemic conditions, and to the cerebral cortex for traumatic brain injury and other CNS conditions (Uri Oron, Intery Cardiol (2011) 3 (6) 627-629; and Margaret Naeser, Photomedicine and Laser Surgery (2011) 29 (7) 443-446, the disclosures of which are incorporated by reference).

More specifically, the present invention provides a light therapy pad that can provide optimum therapeutic benefit for use on a patient's shin for illuminating the stem cells within the marrow of the tibia and optimized for use on the patient's forehead for illuminating the cerebral cortex of the brain.

Recent peer-reviewed articles have shown benefits from illuminating stem cells of a patient shortly after a traumatic event such as traumatic brain injury, myocardial infarct, or stroke. The challenge is irradiating the stem cells of the patient in-vivo. We have determined through laboratory measurements that the tibia offers an optical window to the marrow of the tibia containing mesenchymal stem cells which are multipotent stem cells with the ability to differentiate into a variety of cell types. FIG. 19 shows a cross-section of the lower leg. The anterior surface of the tibia is flat, thin and covered only with dermis. Textbook values of optical attenuation of bone and dermis indicate that light from 630 nm through 900 nm would be minimally attenuated through optical scattering and the tibia's marrow could be reasonably illuminated in-vivo. Testing has verified this hypothesis.

The design of the light therapy pad for use with the tibia is shaped physically to coincide with the exposed surface of the tibia and includes a mechanical securement mechanism, described hereinafter, to keep the light pad securely in place over the tibia. Due to the limited exposed area of the tibia and the high light absorption of the muscle on either side of the tibia's exposed surface, it is important, and possibly essential, that the light therapy pad stay securely positioned in the required position.

The design of the brain frontal cortex pad is physically shaped to coincide with the exposed surface of the forehead, and includes an adhesive mechanism, such as a tacky silicone coating described hereinafter, for adhering the therapy pad to the patient's forehead.

An example of an LED and electrical tracing layout of a light therapy pad for a tibia bone marrow treatment is shown in FIG. 20. An example of an LED and electrical tracing layout of a light therapy pad for a cerebral cortex treatment is shown in FIG. 22.

FIG. 20 shows an elongated therapy device 121 that includes an AC power source 5 with positive current drive (+) and negative current drive (−) cycles, and a plurality of rows of LEDs 151-159 arranged as approximate linear tracings, each comprising a plurality of LEDs 10 and first and second header tracings 12a and 12b. The plurality of LEDs are arranged alternatingly so that about half allow the flow of current in the forward direction during the positive drive cycle (black LED circles shown illuminated during the positive drive cycle), while the remaining LEDs only allow the flow of current during the negative drive cycle (not shown). The circuit includes a standard linear tracing 60 that runs between the AC source 5 and the right side of the row of LEDs 151.

FIG. 21 shows during the positive drive cycle the cumulative net current flows 115*a* through 115*j*, wherein current flow 115*a* is the current flow through standard linear tracing 60, current flow 115*b* is the cumulative net current flow through row of LEDs 151, current flow 115*c* is the cumulative net current through row of LEDs 152, current flow 115*d* is the cumulative net current flow through row of LEDs 153, etc. In addition to emitting therapeutical doses of light, the opposite direction cumulative net current flows can effect induced eddy currents within the body tissue when the AC-powered device is placed adjacent to the skin.

FIG. 22 shows a rectangular therapy device 221 that includes an AC power source 5 with positive current drive (+) and negative current drive (−) cycles, and a plurality of rows of LEDs 251-257 arranged as approximate linear tracings, each comprising a plurality of LEDs 10 and first and second header tracings 12*a* and 12*b*. The plurality of LEDs are arranged alternatingly so that about half allow the flow of current in the forward direction during the positive drive cycle (black LED circles shown illuminated during the positive drive cycle), while the remaining LEDs only allow the flow of current during the negative drive cycle (not shown).

FIG. 23 shows during the positive drive cycle the cumulative net current flows 215*a* through 215*j*, wherein current flow 215*a* is the cumulative net current flow through row of LEDs 251, current flow 215*b* is the cumulative net current through row of LEDs 252, current flow 215*c* is the cumulative net current flow through row of LEDs 253, and so on for rows of LEDs 254-256. While rows of LEDs 251-256 are arranged to effect cumulative net current flow in alternating directions, the column 257 of rows of LEDs are all arranged with co-directions cumulative net current flow. In addition to emitting therapeutical doses of light, the opposite-direction cumulative net current flows can effect induced eddy currents within the body tissue when the AC-powered device is placed adjacent to the skin.

Attachment Means for a Light Therapy Pad

A device for attaching a light therapy pad to a body part can include a mechanical securement, for example for attachment to limbs, such as an arm and leg, or an adhesive securement, for example for attachment to a core portion of the body, such as the head and trunk.

A mechanical securement can consist of a layered, flexible stainless steel bi-stable spring band sealed within the soft flexible layers of the light therapy pad structure. The bi-stable spring band can be straightened out, creating tension within the band. Gently pressing the band against the user's convex body curvature causes the band to spring back into a curve or coil that wraps the therapy pad around the wrist, arm, leg, etc, quickly and gently securing the light pad to the user.

Figure 24:
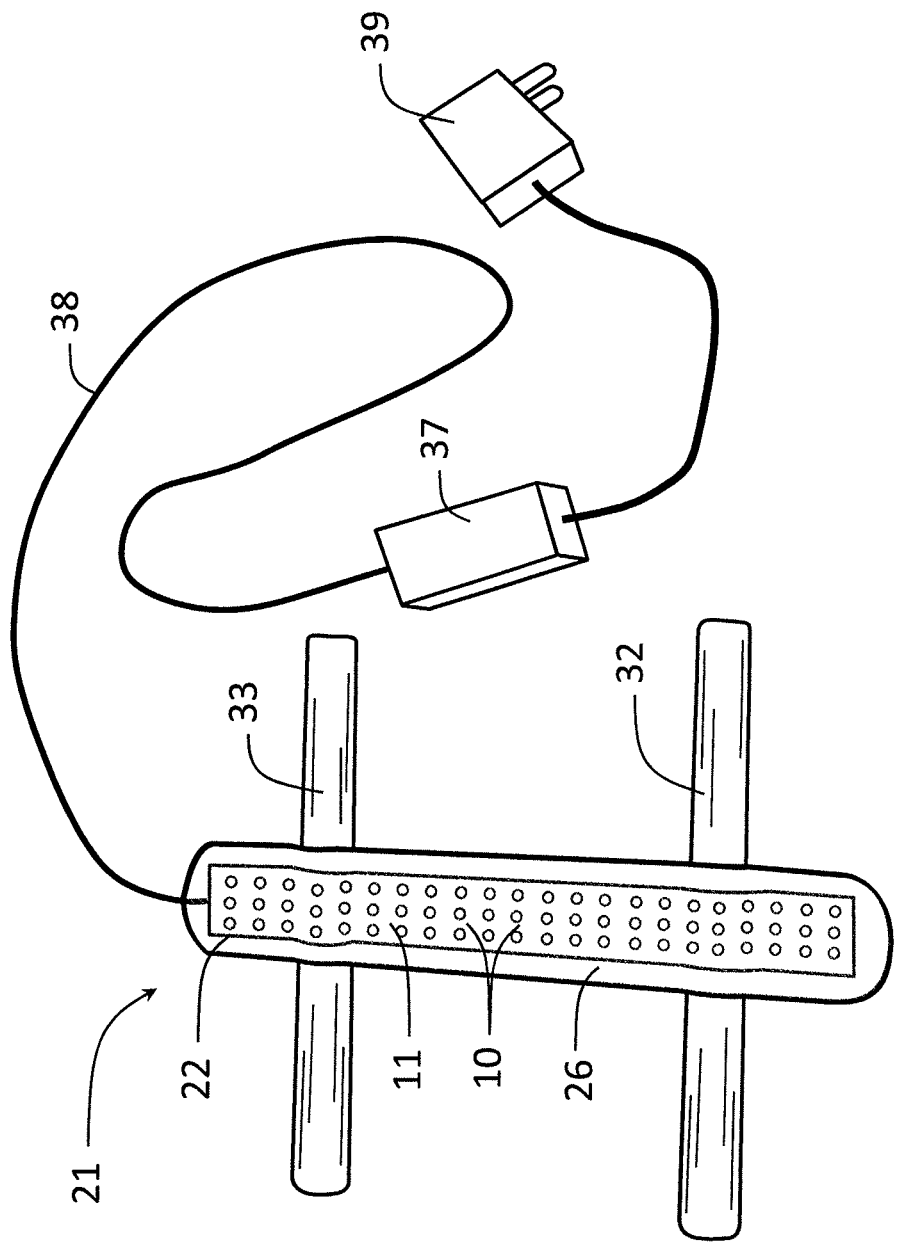
FIG. 24 shows a therapy pad including a mechanical securement device.

FIG. 24 shows an embodiment of a light therapy pad including a mechanical securement device. The therapy pad includes a structure 21 including an array 11 of LEDs 10, and a skin-facing, transparent layer 22 overlying the array 11 and extending into the side margins 26. A pair of bi-stable spring bands 32 and 33 is attached, typically adhesively, to the outer, heat dissipating layer 24 of the pad, near the opposed ends of the pad. The bi-stable spring bands 32, 33 are oriented transverse the elongated dimension of the pad, so that the bands 32, 33 curl toward the skin-facing direction when uncoiled. The LEDs are connected to a controller 37 via electric wiring 38, and is powered by mains power via a standard mains plug 39.

Figure 25:
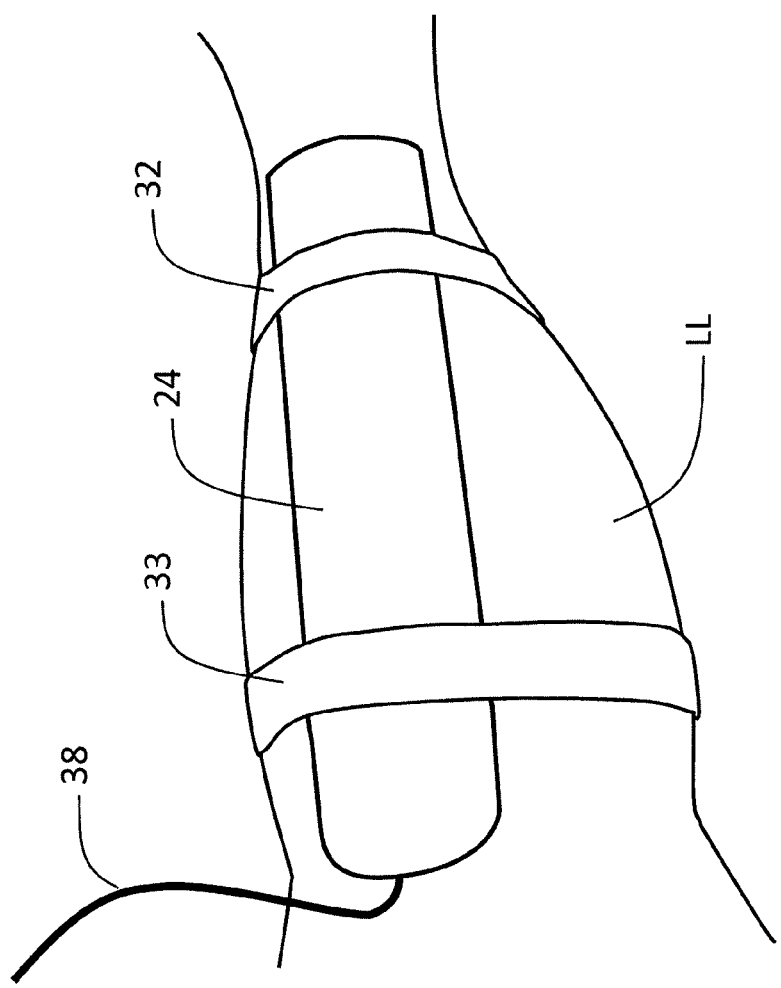
FIG. 25 shows the therapy pad of FIG. 24 secured to the lower leg of a patient.

FIG. 25 shows the therapy pad secured to the lower leg (LL) of a patient, with the bands 32,33 uncoiled and wrapped around the leg.

The light therapy pad can also employ an adhesive mechanism for securing the pad to the body. The skin-facing layer of transparent silicone provides some tack that helps to keep the pad in skin-contacting proximity to the lower leg (LL), with the array of LEDs disposed directly over the tibia. To improve the tack securement of the pad to the body, a tacky silicone coating available commercially, for example, as the Slacker® (Smooth-On Corp.) can be applied over the transparent layer 22 to provide enhanced adhesion. This attachment technique is medically approved. Light therapy devices for the forehead, sternum, and other body core locations can also utilize the adhesion of tacky silicone material.

The Light Therapy pad of the present invention can include any one or more of the following features: control of the intensity and duration of the light therapy dose; electronic temperature feedback design, thermal conduction design, body attachment mechanism; use of reverse-mounted LEDs to achieve a structure having thinness, smoothness, and flexibility; and shaping of the structure to correspond to specific anatomical sites to achieve specific therapeutic outcomes.

I claim:

1. A light and bioelectric therapy pad for providing light stimulation and bioelectric stimulation to adjacent bodily tissue, including:
   a) a pad substrate;
   b) two or more light emitting diodes (LEDs) arranged in a matrix and positioned on the pad substrate, each of the two or more LEDs having an anode and a cathode, the matrix of two or more LEDs including a plurality of spacially parallel and spaced-apart rows of LEDs, each row of LEDs having a first end and an opposite second end, and including more than two LEDs positioned from the first end to the second end of the row, and including a first group of LEDs and a second group of LEDs,
   c) a first header tracing extending proximate to, along one side of, and parallel with each row of LEDs, from the first end to the opposite second end, and a second header tracing extending proximate to, along the opposite side of, and parallel with each row of LEDs, from the first end to the opposite second end;
   d) wiring to connect the anode and cathode of each LED of each row of LEDs in parallel between the respective first header tracing and the second header tracing, wherein the first group of the LEDs is wired with the anode to the first header tracing and the cathode to the second header tracing, and the second group of LEDs is wired with the cathode to the first header tracing and the anode to the second header tracing;
   e) where each row of more than two LEDs, respective first and second header tracings, and wiring to connect each LED to said first and second header tracings, forms an approximate linear tracing (ALT) having a first end and a second end, and a centerline, and where the plurality of spacially parallel and spaced-apart rows of LEDs, respective first and second header tracings, and wiring to connect each LED to said first and second header tracings, form a plurality of ALTs in a parallel, side-by-side pattern having a spacing between centerlines of at least 4 mm;
   f) a first current supply tracing connected to the first header tracing at the first end of each ALT, and a second current supply tracing connected to the second header tracing at the opposite second end of each ALT, where the plurality of ALTs are wired in series, with a first current supply tracing of a first ALT wired to a second current supply tracing of a second ALT;

g) an AC source connected to the plurality of ALTs;

h) were a current flowing from the first current supply tracing to the second current supply tracing, during the positive drive cycle of the AC, flows through only the first group of LEDs and through both the first header tracing and the second header tracing in the same direction from the first end of the ALT to the second end of the ALT, resulting in light being emitted only from the first group of LEDs and in a unidirectional flow of current through the ALT from the first end to the second end, and in a magnetic field in a first direction around the ALT in accordance with Ampere's law;

i) where a current flowing from the second current supply tracing to the first current supply tracing, during the negative drive cycle of the AC, flows through only the second group of LEDs and through both the first header tracing and the second header tracing in the same direction from the second end of the ALT to the first end of the ALT, resulting in light being emitted only from the second group of LEDs and in a unidirectional flow of current through the ALT from the second end to the first end, and in a magnetic field in an opposite second direction around the ALT in accordance with Ampere's law;

j) where the oppositely-directed magnetic fields of an adjacent pair of ALTs during alternating positive drive cycles and negative drive cycles of the AC, induce eddy currents within a body tissue when the light and bioelectric therapy pad is placed adjacent the skin of a subject; and k) a light-transmissive, thermally-insulative, skin-facing film layer disposed over the pad substrate, through which the emitted light of the plurality of LEDs can pass.

2. The light and bioelectric therapy pad according to claim 1, wherein the first current supply tracing is connected to the first header tracing before a first connection of the first header tracing to a first LED in the row of LEDs, and the second current supply tracing is connected to the second header tracing before a first connection of the second header tracing to a last LED in the row of LEDs.

3. The light and bioelectric therapy pad according to claim 1, wherein a cumulative current capacity flowing through the first group of LED during a positive drive cycle and a cumulative current capacity flowing through the second group of LED during a negative drive cycle are substantially the same.

4. The light and bioelectric therapy pad according to claim 3, wherein the AC source has a peak current output of about 1 amp, and a spacing between adjacent spaced-apart ALT is up to about 1.4 cm.

5. The light and bioelectric therapy pad according to claim 1, wherein the plurality of LEDs emit light within the visible through near infrared wavelength range.

6. The light and bioelectric therapy pad according to claim 5, further including a temperature sensor for sensing the pad/skin interface temperature, and a controller for closed loop control of the current output of the AC source based on the pad/skin interface temperature.

7. The light and bioelectric therapy pad according to claim 1, wherein the therapy pad has a shape that corresponds, contours to, or registers with an anatomical site of a mammalian body.

8. The light and bioelectric therapy pad according to claim 7, wherein the therapy pad further includes a body attachment mechanism for attaching the therapy pad to a portion of the mammalian body, the body attachment mechanism selected from the group consisting of a mechanical attachment mechanism and an adhesive attachment mechanism.

9. The light and bioelectric therapy pad according to claim 1, further including an electronic control system that delivers a therapeutically-effective total light dosage by monitoring and controlling the current flow through the plurality of ALT.

10. The light and bioelectric therapy pad according to claim 1, further including an optically opaque outer layer that extends beyond the edge of the light emitting LEDs, to contain effectively all light given off by the LEDs from passing out a side of the therapy pad.

11. An approximate linear tracing (ALT) that directs current flow in one direction along the ALT during a positive drive cycle of an alternating current (AC), and current flow in an opposite direction along the ALT during a negative drive cycle of the AC, the ALT including a plurality of light emitting diodes (LEDs) arranged in a row having a first end and an opposite second end, the plurality of LEDs including a first group of a plurality of LEDs and a second group of plurality of LEDs, a first header tracing extending proximate to, along one side of, and parallel with the row of LEDs from the first end to the opposite second end, and a second header tracing extending proximate to, along the opposite side of, and parallel with the row of LEDs from the first end to the opposite second end, wiring to connect an anode and a cathode of each LED of the row of LEDs in parallel between the first header tracing and the second header tracing, wherein the first group of the LEDs is wired with the anode to the first header tracing and the cathode to the second header tracing, and the second group of the LEDs is wired with the cathode of to the first header tracing and the anode to the second header tracing, and further including a first current supply tracing connected to the first header tracing at the first end of the row of LEDs, and a second current supply tracing connected to the second header tracing at the opposite second end of the row of LEDs.

12. The ALT according to claim 11, wherein the first current supply tracing is connected to the first header tracing before a first connection of the first header tracing to a first LED in the row of LEDs, and the second current supply tracing is connected to the second header tracing before a first connection of the second header tracing to a last LED in the row of LEDs.

13. A method for light stimulation and bioelectric stimulation to adjacent bodily tissue, comprising the steps of:

a) applying a light and bioelectric therapy pad according to claim 1 to a body portion of a patient, the plurality of ALT including a first ALT and an adjacent second ALT, b) energizing the AC current source, c) effecting current flow in the first ALT in a first direction during the positive drive cycle of the AC to generate a magnetic field in a first direction around the first ALT in accordance with Ampere's law, and in a second direction, opposite the first direction, during the negative drive cycle of the AC to generate a magnetic field in a second direction around the first ALT in accordance with Ampere's law, d) effecting current flow in the adjacent second ALT in the second direction during the positive drive cycle of the AC to generate a magnetic field in a second direction around the second ALT in accordance with Ampere's law, and in the first direction during the negative drive cycle of the AC to generate a magnetic field in a first direction around the second ALT in accordance with Ampere's law, and e) emitting light from the first group of the plurality of LEDs of the first ALT and of the second ALT during the positive drive cycle of the AC, and emitting light from the second group of the plurality of LEDs of the first ALT and of the second ALT during the negative drive cycle of the AC, wherein the current flows in the opposite first and second directions in the first ALT and adjacent second ALT during both the positive drive cycle and the negative drive cycle of the AC, and the magnetic fields generated in the opposite first and second directions around the first ALT and adjacent second ALT, during both the positive drive cycle and the negative drive cycle of the AC, induces therapeutic eddy currents within the tissue of the body portion.

14. The method for light stimulation and bioelectric stimulation according to claim 13, further including an electronic control system for delivering a therapeutically-effective total light dosage of the light emitted from the plurality of LEDs, including the step of monitoring and controlling the current flow through the electrical tracing circuit.

15. The light and bioelectric therapy pad according to claim 1, wherein the skin-facing film layer has a thickness of about 0.5 mm to about 5 mm.

16. The light and bioelectric therapy pad according to claim 1, wherein the spacing between adjacent ALTs is up to about 14 mm.

17. The light and bioelectric therapy pad according to claim 1, further including a standard linear tracing having a first end and a second end, positioned spatially in parallel, and wired in parallel, with adjacent ALTs.

* * * * *